United States Patent
Huynh-Ba et al.

Patent Number: 5,179,101
Date of Patent: Jan. 12, 1993

[54] ANISOTROPIC COMPOUNDS HAVING NEMATIC PHASE AND LIQUID CRYSTAL MIXTURES

[75] Inventors: Tuong Huynh-Ba, Baden; Maged A. Osman, Zürich, both of Switzerland

[73] Assignee: Merck Patent GmbH, Darmstadt, Fed. Rep. of Germany

[21] Appl. No.: 477,490

[22] Filed: Feb. 9, 1990

Related U.S. Application Data

[60] Division of Ser. No. 800,920, Nov. 25, 1985, which is a continuation of Ser. No. 457,567, Jan. 13, 1983, abandoned.

[30] Foreign Application Priority Data

Jan. 14, 1982 [CH] Switzerland ............ 198/82-0
Jan. 19, 1982 [CH] Switzerland ............ 292/82-3
May 4, 1982 [CH] Switzerland ............ 2725/82-7

[51] Int. Cl.$^5$ ............ C07D 239/30; C07D 239/32; C07D 239/46; C07D 239/47
[52] U.S. Cl. ............ 544/296; 544/315; 544/316; 544/318; 544/322; 544/332; 544/335; 544/298; 544/330
[58] Field of Search ............ 544/242, 296, 298, 315, 544/316, 318, 322, 330, 332, 335

[56] References Cited

U.S. PATENT DOCUMENTS

| | | | |
|---|---|---|---|
| 3,660,404 | 5/1972 | Otterstedt et al. | 544/296 |
| 3,997,536 | 12/1976 | Boller et al. | 544/334 |
| 4,062,798 | 12/1977 | Boller | 252/299.61 |
| 4,146,647 | 3/1979 | Lafon | 544/315 |
| 4,273,929 | 6/1981 | Boller | 544/242 |
| 4,309,539 | 1/1982 | Boller | 544/242 |
| 4,414,221 | 11/1983 | Parsons | 514/383 |
| 4,427,437 | 1/1984 | Serban et al. | 71/92 |
| 4,439,015 | 3/1984 | Rich et al. | 350/350 R |

FOREIGN PATENT DOCUMENTS 755997  8/1956  United Kingdom.

OTHER PUBLICATIONS

Schubert, H, Chemical Abstracts, 75:98467d (1970).
Schubert, H, Chemical Abstracts, 73:98890 (1970).
Zaschke, H., Chemical Abstracts, 83:193218 (1975).
Allen, David W et al., Chemical Abstracts, 93:149,282w (1980).

Primary Examiner—Mukund J. Shah
Assistant Examiner—Matthew V. Grumbling
Attorney, Agent, or Firm—Oblon, Spivak, McClelland, Maier & Neustadt

[57] ABSTRACT

Anisotropic compounds having a nematic phase have the formula (1)

wherein A is a cyclic radical selected from the group consisting of

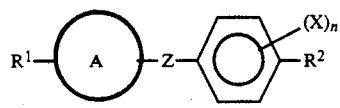

(10)

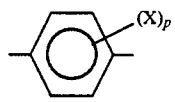

(11)

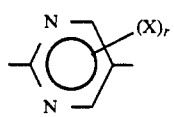

(12)

Z is selected from the group consisting of a single bond, a —CH2CH2— group, a methyleneoxy group and an oxymethylene group, n is 1 or 2,
p is 0, 1, or 2,
r is 0 or 1,
X is selected from the group consisting of fluorine, chlorine, bromine, iodine, nitrile and methyl,
$R^1$ and $R^2$ are selected from the group consisting of hydrogen, $C_1$–$C_{12}$-alkyl, $C_1$–$C_{12}$-alkoxy, $C_1$–$C_{12}$-alkanoyloxy and $C_1$–$C_{12}$-alkylamino and cyclic groups of the formulas

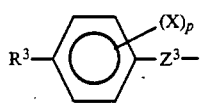

(13)

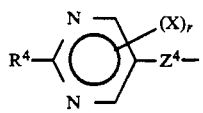

(14)

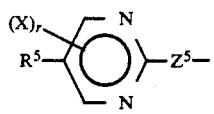

(15)

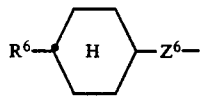

(16)

wherein $R^3$ through $R^6$ are selected from the group consisting of hydrogen, $C_1$–$C_{12}$-alkyl, $C_1$–$C_{12}$-alkoxy, (Abstract continued on next page.)

$C_1$-$C_{12}$-alkanoyloxy, and $C_1$-$C_{12}$-alkylamino, and $Z^2$ through $Z^6$ represent a Z group, with the provisos that:
(A) none of the above aromatic radicals (10), (11), (13), (14) or (15) is directly bonded to the C-atom of a methyleneoxy or oxymethylene group; and
(B) at least one X group is methyl when only one or none of the groups $R^1$ and $R^2$ is a cyclic radical of formulas (13) or (16), A has the formula (12), Z is a single bond, and any of $Z^3$ or $Z^6$, if present, is a single bond.

Compounds having the defined lateral substituents on the rings have a reduced tendency to form smectic phases as compared with the compounds not having such lateral substituents.

27 Claims, No Drawings

ANISOTROPIC COMPOUNDS HAVING NEMATIC PHASE AND LIQUID CRYSTAL MIXTURES

This is a division of application Ser. No. 06/800,920, filed on Nov. 25, 1985 which is a continuation of 06/457,567, filed Jan. 13, 1983 now abandoned.

BACKGROUND OF THE INVENTION

1. Field of the Invention

This invention relates to compounds having a positive dielectric anisotropy which have liquid-crystalline properties, and more particularly to such compounds which have a nematic mesophase.

2. Description of the Prior Art

Liquid crystal displays using twisted nematic cells, also known as TN-displays require, as is well-known, nematic liquid-crystalline materials having a positive anisotropy of the dielectric constant, also indicated as a positive DCA. The DCA, or $\Delta\epsilon$, defined as $\Delta\epsilon = \epsilon_{\parallel} - \epsilon_{\perp}$ wherein $E_{\parallel}$ is the dielectric constant (DC) parallel to the long axis of the molecule and $\epsilon_{\perp}$ is the DC perpendicular to the molecular axis.

For multiplexed operation of these cells it is also desirable that the LC-material have a characteristic curve exhibiting the steepest possible contrast, i.e., the greatest possible change of the light absorption properties with change of the applied electric field. This can be attained by optimizing two criteria used in choosing the available anisotropic materials, namely (a) the smallest possible value of the ratio of the elastic constants of bending and of expansion, also indicated as $k_{33}/k_{11}$, and (b) by the smallest possible value of the ratio of the DCA ($\Delta\epsilon$) to the DC perpendicular to the nematic axis ($\Delta_{\perp}$), i.e., of $\Delta\epsilon/\epsilon_{\perp}$. The particulars of these requirements can be found in the literature: Gharadjedagji, F. et al., Rev. Phys. Appl., 11 (1976), 467; Metz, A. R., SID Digest, Techn. Papers IX (1978), 70 and Alt, P. M. et al., IEEE Trans. El. Dev. Ed. (1974), 146.

At present, two types of anisotropic compounds are available from which to select suitable anisotropic compounds by the above criteria. Each type may contain two or three rings, and they have the following structure:

Type I:

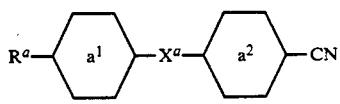

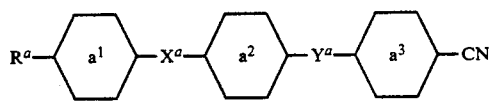

Type II:

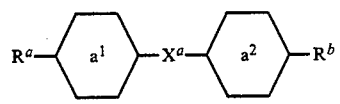

und

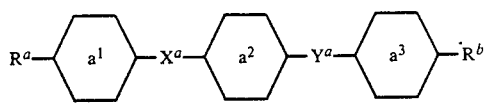

wherein $a^1$, $a^2$ and $a^3$ are aromatic, heteroaromatic or cycloaliphatic rings, such as benzene, pyrimidine, and trans-cyclohexane rings; $X^1$ and $Y^a$ are so-called bridge groups such as —COO—, —CH=N—, —CH$_2$O—, —N=N—, —CH$_2$CH$_2$— or a single bond and $R^a$, $R^b$ are so-called terminal groups, such as alkyl, alkoxy, alkanoyloxy, or alkylamino groups, which contain an alkyl portion having in general 1 to 12 C atoms in a straight or branched chain.

Type I substances, because of their relatively large polarity $R^a$/CN in the direction of the long axis of the molecule (the nematic axis or director) offer a high positive DCA-value and a correspondingly low threshold voltage. However, they have high $\Delta\epsilon/\epsilon_{\perp}$-values, which is disadvantageous for multiplex operation and also have a comparatively high $k_3/k_{11}$-value which is also disadvantageous for this purpose. The contrast characteristic curve of these substances is relatively weak,.

Type II substances are slightly polar or nonpolar and have $\Delta\epsilon/\epsilon_{\perp}$-values necessary for a steep characteristic curve, and $k_{33}/k_{11}$-values in comparison with substances of Type I (at comparable chain length). Furthermore, the viscosity of Type II substances is less than that of Type I substances.

For all these reasons, anisotropic substances of Type II are indispensible components of LC-mixtures for multiplex operation of TN-displays.

However, a significant disadvantage of the known anisotropic substances of Type II is their pronounced tendency to form smectic phases, especially when these materials have relatively long terminal groups, e.g., when they have alkyl groups of a certain length. This can be seen by referring to the values in the literature, e.g. in "Liquid Crystals in Tables," VEB Deutscher Verlag, Leipzig, 1974.

The appearance of smectic phases in anisotropic compounds narrows the range of the nematic phase which alone is suitable for TN-displays or completely eliminates it.

Therefore, a need has continued to exist for anisotropic compounds of Type II having a reduced tendency to form smectic phases.

SUMMARY OF THE INVENTION

Accordingly, it is an object of the invention to provide anisotropic compounds of Type II wherein the tendency to form smectic phases is decreased or eliminated.

A further object is to provide compounds of this type which in general possess a nematic phase or which have a greater temperature range of the nematic phase for comparable structures.

Further objects of the invention will become apparent from the description of the invention which follows.

It has now surprisingly been found that the objects of the invention can be attained by an accurately defined group of Type II compounds containing at least one so-called lateral substituent on the ring in the fundamental structural formula.

The compounds of the invention are anisotropic compounds having a nematic phase having the formula

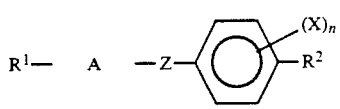  (1)

wherein A is a cyclic radical selected from the group consisting of

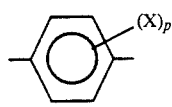  (10)

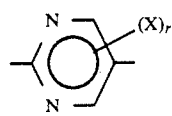  (11)

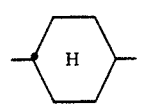  (12)

Z is selected from the group consisting of a single bond, a —CH$_2$CH$_2$— group, a methyleneoxy group and an oxymethylene group,
n is 1 or 2,
p is 0, 1, or 2,
r is 0 or 1,
X is selected from the group consisting of fluorine, chlorine, bromine, iodine, nitrile and methyl,
R$^1$ and R$^2$ are selected from the group consisting of hydrogen, C$_1$–C$_{12}$-alkyl, C$_1$–C$_{12}$-alkoxy, C$_1$–C$_{12}$-alkanoyloxy and C–C$_{12}$-alkylamino and cyclic groups of the formulas

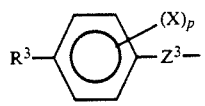  (13)

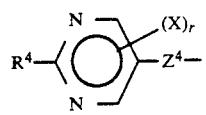  (14)

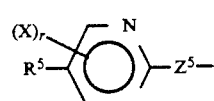  (15)

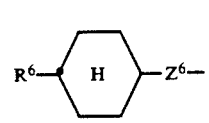  (16)

wherein R$^3$ through R$^6$ are selected from the group consisting of hydrogen, C$_1$–C$_{12}$-alkyl, C$_1$–C$_{12}$-alkoxy, C$_1$–C$_{12}$-alkanoyloxy, and C$_1$–C$_{12}$-alkylamino, and Z$^2$ through Z$^6$ represent a Z group, with the provisos that:

(A) none of the above aromatic radicals (10), (11), (13), (14) or (15) is directly bonded to the C-atom of a methyleneoxy or oxymethylene group; and (B) at least one X group is methyl when only one or none of the groups R$^1$ and R$^2$ is a cyclic radical of formulas (13) or (16), A has the formula (12), Z is a single bond, and any of Z$^3$ or Z$^6$, if present, is a single bond.

DETAILED DESCRIPTION OF THE INVENTION AND PREFERRED EMBODIMENTS

The new Type II anisotropic compounds of the invention having a nematic phase have the formula (I)

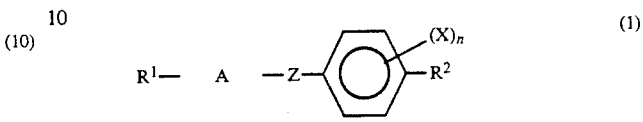  (1)

wherein A signifies a cyclic radical having one of the formulas (10), (11) or (12)

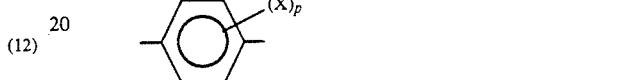  (10)

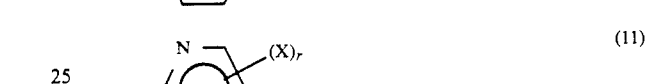  (11)

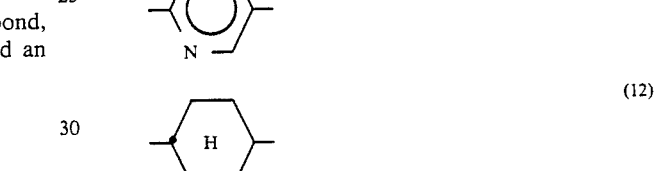  (12)

wherein the formula (11) can be a pyrimidine ring bonded in either the 2,5-positions or in the 5,2-positions.

The cyclic radical of formula (12) always has the trans-configuration as shown by the dot, provided that R$^1$ is not a hydrogen atom, which would eliminate the possibility of cis/trans-isomers.

The bridge member Z in formula (1) indicates a single bond, an ethylene group (—CH$_2$CH$_2$—), a methyleneoxy (—CH$_2$O—), or an oxymethylene group (—COH$_2$—), insofar as these are not excluded by the conditions which follow.

The numerical indices have the following significance: n is 1 or 2; p is 0, 1 or 2; r is 0 or 1.

The most important groups for the lateral substituent X (one or more) are halogen, i.e., fluorine, chlorine, bromine or iodine, or methyl (—CH$_3$) or nitrile (—CN). If the molecule of formula (1) has several lateral substituents X, these can be the same or different.

Thus, the following conditions apply for compounds of formula (1) of the invention:

(A) When an aromatic radical of the formula (10), (11), (13), (14) or (15) is present in a molecule of formula (1), a methyleneoxy or oxymethylene group is never directly bonded to a C-atom of one of these radicals; in other words, the molecule of formula (1) should not contain any group of the formula

wherein Ar represents a cyclic radical of the formula (10), (11), (13), (14) or (15). It has been determined that benzylethers of this type and similar compounds having a group of the formula

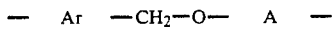
— Ar —CH$_2$—O— A — wherein Ar and A have the above meaning, tend to product instability when used as liquid crystals or in mixtures of liquid crystals.

(B) Furthermore the new compounds of formula (1) of the invention have the proviso that at least one X in the molecule of formula (1) is methyl, when only one or none of the groups R$^1$, R$^2$ is a cyclic radical of the formula (13) or (16). Accordingly, A has the formula (12) and the bridge member Z as well as the optionally present bridge members Z$^3$ or Z$^6$ represent single bonds.

For many purposes it is further preferred that the cyclic radical of the formula (12) or the cyclic radical of the formula (16) each should be not at the same time be bonded on one side to an oxygen atom and on the other side to an oxygen atom or nitrogen atom. Finally it is preferred for especially stable compounds of the formula (1) that the aromatic rings not lie between two oxygen atoms which are directly bonded to a ring, especially when a lateral substituent X=CN is attached to this ring.

R$^1$ and R$^2$ can be the same or different and signify hydrogen, alkyl, alkoxy, alkanoyloxy (Alk—C-(O)—O—) or alkylamino (Alk—N(H)—) having 1 to 12 C-atoms in the alkyl portion; the alkyl portion can be linear or branched and may optionally be chiral; R$^1$ and/or R$^2$ can also be cyclic groups of the formula (13) to (16):

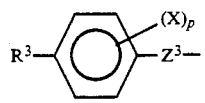
(13)

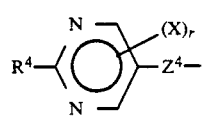
(14)

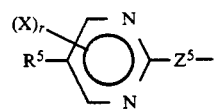
(15)

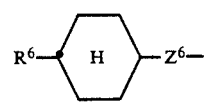
(16)

In the formulas (13) to (16) the terminal groups R$^3$ to R$^6$ have the significance given above for the noncyclic R$^1$ and R$^2$; X, p and r are as given above and the bridge groups X$^3$ through X$^6$ have one of the meanings given for Z, whereby in a molecule of formula (1) the significance of Z on the one hand and Z$^3$ through Z$^6$ on the other can be the same or different.

The new compounds of formula (1) of the invention can in general be dinuclear, trinuclear or tetranuclear. Prefererd compounds of the invention have the formulas (22) to (33) as illustrated and defined in claims 2-13.

The invention also includes liquid crystal mixtures which contain at least one compound of formula (1), e.g., one or more compounds of formulas (22) to (33). This will be further explained below.

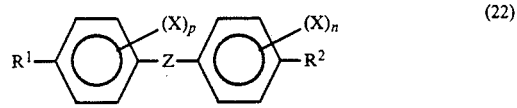
(22)

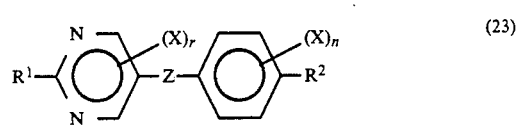
(23)

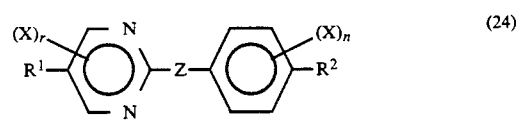
(24)

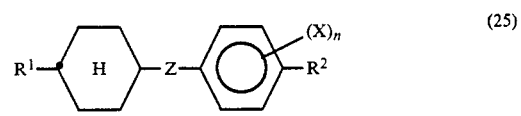
(25)

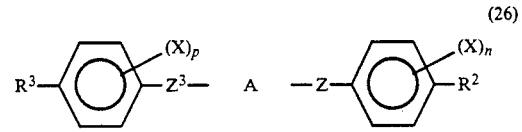
(26)

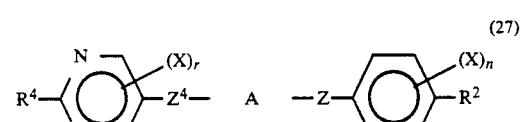
(27)

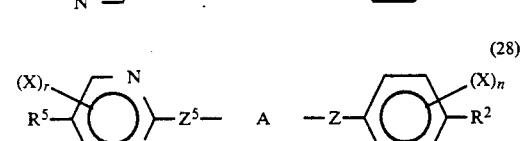
(28)

(29)

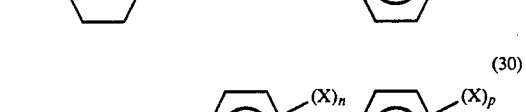
(30)

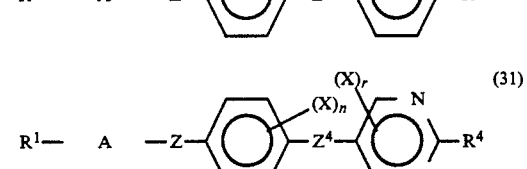
(31)

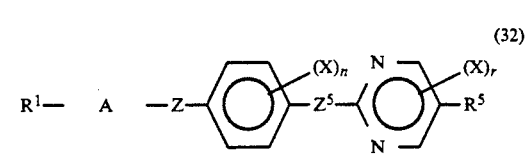
(32)

-continued

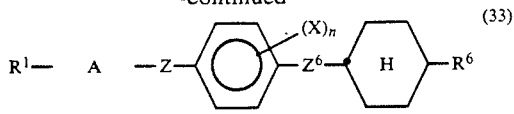

In a preferred group of compounds of the invention X is a methyl group. In another preferred group of compounds of the invention X is fluorine, chlorine, bromine or iodine, wherein fluorine and chlorine are especially preferred. In another preferred group of compounds of the invention X is a nitrile group.

If the compound of formula (1) has a large transverse dipole moment, which can result, e.g., when two or more X's, such as nitrile and/or halogen are present, the compound generally also has a strongly negative Δε and can then be used, e.g., for liquid crystal displays which operate by the so-called inverse guest/host-effect, or for certain types of dynamic scattering cells, DAP-devices and HN-devices. The compounds of the invention contain at least one lateral substituent, X; however they also can have two or more lateral substituents X, wherein the particular molecule of formula (1) can bear different or identical lateral substituents X, e.g., methyl and halogen, methyl and nitrile, halogen and nitrile or methyl and halogen and nitrile.

The new compounds of formula (1) of the invention are based on the discovery that it is important for avoiding or suppressing the tendency to form smectic phases in certain compounds of Type II that the lateral substituent or substituents must have a certain volume but not too great a volume. The lower limit of the volume of the lateral substituents suitable for use according to the invention depends on the tendency of the fundamental structure II (i.e., formula (1) without lateral substituents X) to form smectic phases. In general, the introduction of one or more lateral substituents X having relatively large volumes in comparison to the corresponding fundamental structure without lateral substituents produces a lowering of the clearing point; for dinuclear compounds of formula (I) the lateral substituents having lesser volumes, namely fluorine, chlorine and methyl are accordingly preferred. The volumes of the substituents X increases in approximately the following sequence:

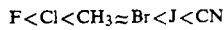

Two synthetic procedures are especially suitable for preparing the compounds (1) or the invention. On the one hand a desired substituent(s) X may be introduced into the corresponding parent compound, e.g., by chlorination or bromination, optionally with subsequent replacement of a substituent X, such as chlorine, by another, such as fluorine, by halogen exchange or by reaction of a corresponding halogen compound with a metal cyanide to introduce the nitrile group. In analogous fashion a carbonyl group can be introduced into the corresponding parent compound, e.g., by catalytic reaction with a formylating reagent, such as oxalyl chloride, and then be reduced to a methyl group.

The other method of synthesis relies on the fact that for construction of the compound (1) component compounds already bearing the corresponding substituents X are used and are linked together, e.g., by condensation.

Furthermore, a compound of the invention can be transformed by conventional methods into another compound of the invention by modification of the terminal groups $R^1$ through $R^6$.

Suitable parent or starting compounds are known or can be obtained by methods analogous to those used for known compounds. Suitable starting compounds having pyrimidine rings are, e.g., described in East German Patent 95,892 and West German OS 26 41 724. The following reaction scheme is presented as a general example of the preparation of the novel anisotropic compounds. The characters have the same general significance as in formula (1).

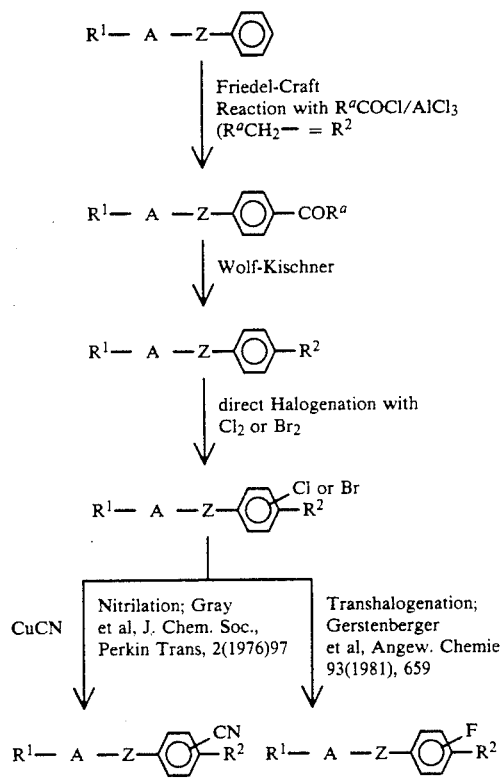

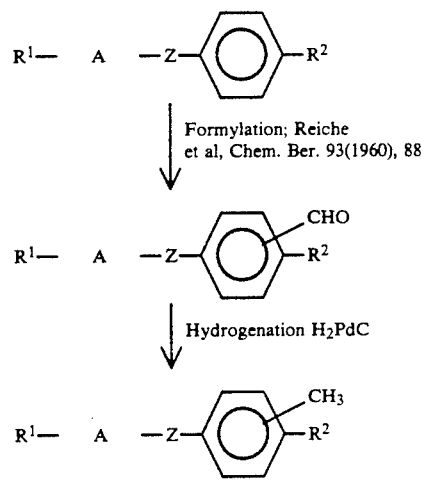

SCHEME C

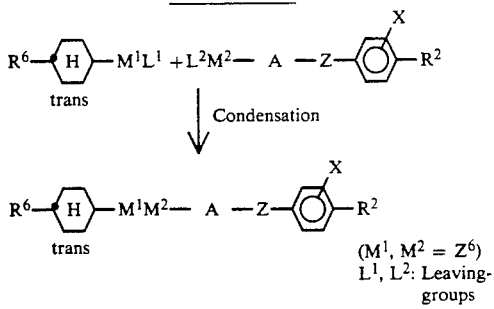

SCHEME D

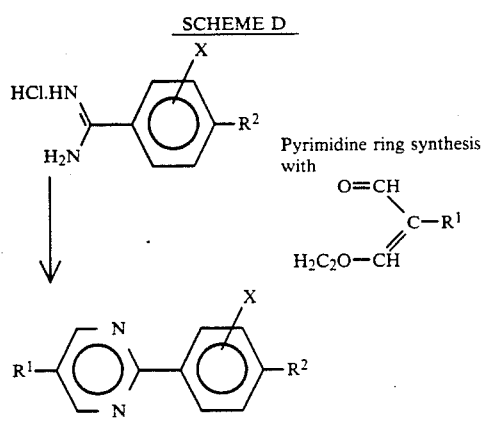

SCHEME E

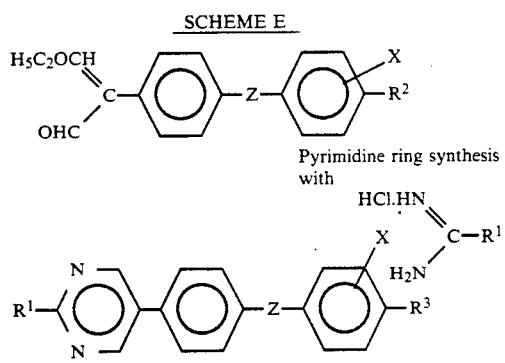

The compounds of formula (1) according to the invention can be used analogously to the known compounds of Type II for LC-mixtures in TN-displays with multiplex operation. They offer the advantage that the problem of smectic phases can be eliminated or significantly reduced.

LC-mixtures according to the invention can be comprised of one or more compounds of the formula (1), e.g., in a total amount up to 60 mole percent, wherein the proportion of individual compounds of formula (1) can comprise up to 30 mole percent of the mixture. The remaining portion of the LC-mixtures according to the invention is for the most part one or preferably more known compounds of Type I.

Having generally described the invention, a more complete understanding can be obtained by reference to certain specific examples which are provided herein for purposes of illustration only and are not intended to be limiting unless otherwise specified. In the following examples the temperature properties of the mesophases are indicated in the conventional way by giving the corresponding temperatures (° C.) between the symbols K (crystalline), S (smectic), N (nematic) and I (isotropic).

EXAMPLE 1

4-Hydroxy-4'-pentyldiphenyl was converted with elemental chlorine to 3-chloro-4-hydroxy-4'-pentyldiphenyl which was then converted by condensation with n-hexyliodide into a compound of formula (1) according to the invention, namely 3-chloro-4-hexyloxy-4'-pentylbiphenyl having the formula (100)

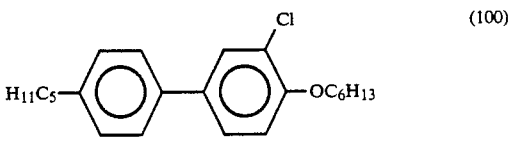

By an analogous procedure without chlorination, however, the comparison compound of formula (101) was prepared.

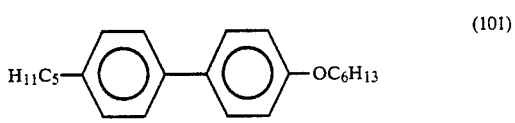

The investigation of the mesophase temperatures gave the surprising result that the compound according to the invention having formula (100) exhibited a pure nematic mesophase having K 1.7 N 11.1 I, while the comparison compound of formula (101) had no nematic phase and was smectic throughout the entire mesophase region, K 82 S 84 I.

EXAMPLE 2

By the procedure described in Example 1 a compound of the invention having formula (200) was prepared

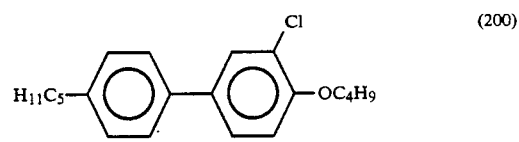

and compared with the corresponding compound not according to the invention having the formula (201).

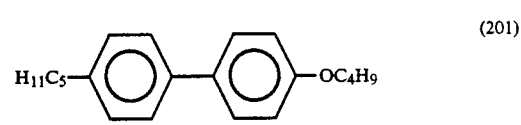

The compound of the invention (200) was monotropically nematic (K 38.1 N (7.5) I), while the comparison compound (201) had only smectic mesophases (K 37 S 801. S 88.1 I).

EXAMPLE 3

The compound of the invention having formula (300), which was prepared by esterification of 3-chloro-4-hydroxy-4'-pentyldiphenyl

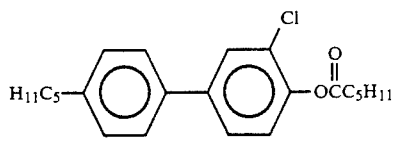

was monotropically nematic (K 22.3 N (-5) I), while the compound not according to the invention having formula (301) exhibited only a smectic mesophase (K 45.7 S 87.4 I).

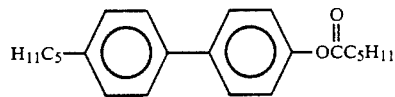

EXAMPLE 4

The new anisotropic compound of the invention having the formula (400)

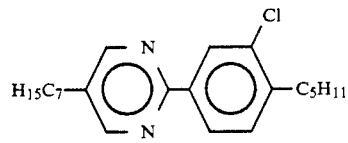

exhibited no smectic phase, while the comparison compound having the formula (401)

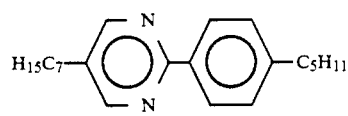

had an exclusively smectic mesophase (K 30.6 S 47.7 I).

EXAMPLE 5

The new anisotropic compound of the invention having the formula (500)

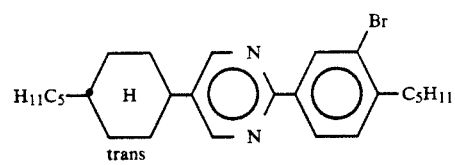

exhibited no smectic phases while the comparative compound not according to the invention having the formula (501) had an exclusively smectic mesophase (K 39.5 S 189.2 I).

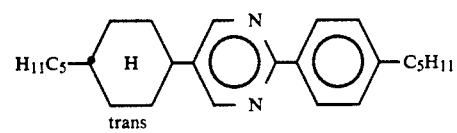

EXAMPLE 6

The new anisotropic compound of the invention having the formula (600)

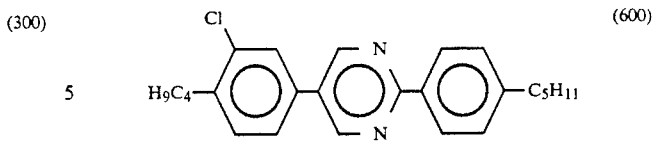

showed no smectic phase (K 111.2 N (103) I), while the comparison compound not according to the invention having the formula (601) had an exclusively smectic mesophase (K 106.4 S 185.2 I).

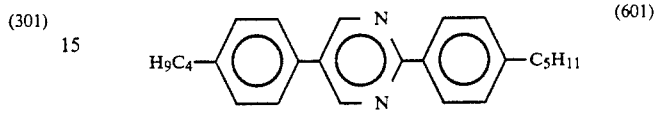

EXAMPLE 7

A cold (about 0° C.) mixture of 16 g of oxayl chloride, 45 g of 1,4-bis(4-trans-pentylcyclohexyl)benzene and 16 g of anhydrous aluminum chloride in 100 ml of symmetrical tetrachloroethane were stirred in a autoclave apparatus until the temperature of the mixture reached about room temperature (10-20 minutes). Then 10 g of anhydrous sodium acetate and 1 g of Pd/C catalyst were added. After the air was purged with nitrogen, hydrogen was introduced to a pressure of 30 bar while the reaction mixture was stirred. After about 120 minutes at this pressure the contents of the autoclave were heated to about 50° C. After 30 minutes at this temperature the reaction mixture was cooled to room temperature and the hydrogen pressure was released, and the autoclave was purged with nitrogen and opened.

The reaction mixture was washed with water, if necessary with cooling, and the separated organic phase was freed of solvent. The residue was recrystallized. The product so obtained, having the formula (700)

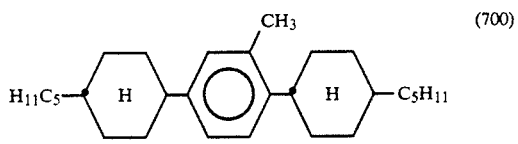

had a melting point of 55.5° C. and exhibited a nematic phase up to 86.5° C.

EXAMPLE 8

The two compounds according to the invention 2'-fluoro-4-butyloxy-4'-pentyldiphenyl and 3'-fluoro-4-butyloxy-4'-pentyldiphenyl exhibit a significant nematic phase while the corresponding compounds not according to the invention, not having fluorine in the 2'- or 3'-position, exhibit no significant nematic phase.

The following compounds can be named as additional compounds of the invention having the formula (1):
2-Fluoro-4,4'-dipropyl-diphenyl
2-Fluoro-4,4'-dipentyl-diphenyl
3-Fluoro-4,4'-dipropyl-diphenyl
3-Fluoro-4,4'-dipentyl-diphenyl
2-Fluoro4-propyl-4'-pentyl-diphenyl
2'-Fluoro-propyl-4'-pentyl-diphenyl
3-Fluoro4-propyl-4'-pentyl-diphenyl
3'-Fluoro4-propyl-4'-pentyl-diphenyl 2-Fluoro-4-pentyl-4'-heptyl-diphenyl
2'-Fluoro-4-pentyl-4'-heptyl-diphenyl
3-Fluoro4-pentyl-4'-heptyl-diphenyl
3'-Fluoro-4-pentyl-4'-heptyl-diphenyl
2-Chloro-4-pentyl-4'-heptyl-diphenyl
2'-Chloro-4-pentyl-4'-heptyl-diphenyl
3-Chloro-4-pentyl-4'-heptyl-diphenyl
3'-Chloro-4-pentyl-4'-heptyl-diphenyl
3-Fluoro-4-butyloxy-4'-pentyl-diphenyl
3-Fluoro-4-hexyloxy-4'-pentyl-diphenyl
3-Fluoro-4-butyloxy-4'-heptyl-diphenyl
3-Fluoro-4-hexyloxy-4'-heptyl-diphenyl
3-Chloro-4-propanoyloxy-4'-heptyl-diphenyl
3-Chloro-4-propanoyloxy-4'-pentyl-diphenyl
3-Chloro-4-propanoyloxy-4'-nonyl-diphenyl
3-Chloro-4-pentanoyloxy-4'-heptyl-diphenyl
3-Fluoro-4-butylamino-4'-pentyl-diphenyl
3-Fluoro-4-hexylamino-4'-pentyl-diphenyl
3-Fluoro-4-butylamino-4'-heptyl-diphenyl
2,5-Difluoro-4,4'-dipentyl-diphenyl
2,5-Difluoro-4,4'-diheptyl-diphenyl
2,5-Difluoro-4,4'-dinonyl-diphenyl
2,5-Dichloro-4,4'-dinonyl-diphenyl
2,5-Difluoro-4-pentyl-4'-heptyl-diphenyl
2,5-Difluoro-4-heptyl-4'-pentyl-diphenyl
3,5-Difluoro-4-butyloxy-4'-pentyl-diphenyl
3,5-Difluoro-4-hexyloxy-4'-pentyl-diphenyl
3,5-Difluoro-4-hexyloxy-4'-heptyl-diphenyl
3,3'-Difluoro-4,4'-dibutyloxy-diphenyl
3,3'-Difluoro-4-butyloxy-4'-hexyloxy-diphenyl
3,3'-Dichloro-4,4'-dihexyloxy-diphenyl
3,3'-Dichloro-4-hexyloxy-4'-octyloxy-diphenyl
3,3'-Difluoro-4,4'-di(butylamino)-diphenyl
3,3'-Dichloro-4,4'-di(hexylamino)-diphenyl
1-(2-Fluoro-4-pentylphenyl)-2-(4-pentylphenyl)-ethane
1-(3-Fluoro-4-pentylphenyl)-2-(4-pentylphenyl)-ethane
1-(2-Chloro-4-heptylphenyl)-2-(4-heptylphenyl)-ethane
1-(3-Chloro-4-heptylphenyl)-2-(4-heptylphenyl)-ethane
1-(3-Fluoro-4-butyloxyphenyl)-2-(4-heptylphenyl)-ethane
1-(3-Chloro-4-hexyloxyphenyl)-2-(4-heptylphenyl)-ethane
1,2-Bis-(2-fluoro-4-pentylphenyl)-ethane
1,2-Bis-(3-fluoro-4-pentylphenyl)-ethane
1,2-Bis-(3-fluoro-4-butyloxyphenyl)-ethane
1,2-Bis-(3-fluoro-4-hexyloxyphenyl)-ethane
1,2-Bis-(3-chloro-4-hexyloxyphenyl)-ethane
1-(3,5-Difluoro-4-butyloxyphenyl)-2-(4-pentylphenyl)-ethane
1-(3-Fluoro-4-pentanoyloxyphenyl)-2-(4-pentylphenyl)-ethane
1-(3,5-Difluoro-4-pentanoyloxyphenyl)-2-(4-pentyl-phenyl)-ethane
2-Fluoro-4-propyl-4'-(4-pentylphenyl)-diphenyl
2-Fluoro-4-pentyl-4'-(4-pentylphenyl)-diphenyl
3-Fluoro-4-pentyl-4'-(4-pentylphenyl)-diphenyl
2-Chloro-4-pentyl-4'-(4-pentylphenyl)-diphenyl
3-Chloro-4-pentyl-4'-(4-pentylphenyl)-diphenyl
2-Bromo-4-pentyl-4'-(4-pentylphenyl)-diphenyl
3-Bromo-4-pentyl-4'-(4-pentylphenyl)-diphenyl
2-Iodo4-pentyl-4'-(4-pentylphenyl)-diphenyl
3-Iodo4-pentyl-4'-(4-pentylphenyl)-diphenyl
2-Cyano-4-pentyl-4'-(4-pentylphenyl)-diphenyl
3-Cyano-4-pentyl-4'-(4-pentylphenyl)-diphenyl
2-Methyl-4-pentyl-4'-(4-pentylphenyl)-diphenyl
3-Methyl-4-pentyl-4'-(4-pentylphenyl)-diphenyl
3-Fluoro-4-butyloxy-4'-(4-pentylphenyl)-diphenyl
3-Chloro-4-butyloxy-4'-(4-pentylphenyl)-diphenyl
3-Bromo-4-butyloxy-4'-(4-pentylphenyl)-diphenyl
3-Iodo-4-butyloxy-4'-(4-pentylphenyl)-diphenyl
3-Cyano-4-butyloxy-4'-(4-pentylphenyl)-diphenyl
3-Methyl-4-butyloxy-4'-(4-pentylphenyl)-diphenyl
3-Fluoro-4-butyloxy-4'-(3-fluoro-4-butyloxyphenyl)-diphenyl
3-Chloro-4-butyloxy-4 -(3-chloro-4-butyloxyphenyl)-diphenyl
3-Bromo-4-butyloxy-4'-(3-bromo4-butyloxyphenyl)-diphenyl
3-Iodo-4-butyloxy-4'-(3-iodo-4-butyloxyphenyl)-diphenyl
3-Methyl-4-butyloxy-4'-(3-methyl-4-butyloxyphenyl)-diphenyl
2-Fluoro-4,4-bis-(4',4''-dipentylphenyl)-benzene
2-Chloro-4,4-bis-(4',4''-dipentylphenyl)-benzene
2-Bromo-4,4-bis-(4',4''-dipentylphenyl)-benzene
2-Iodo-4,4-bis-(4',4''-dipentylphenyl)-benzene
2-Cyano-4,4-bis-(4',4''-dipentylphenyl)-benzene
2-Methyl-1,4-bis-(4',4''-dipentylphenyl)-benzene
2,5-Difluoro-4,4-bis-(4',4''-dipentylphenyl)-benzene
2,5-Dichloro-4,4-bis-(4',4''-dipentylphenyl)-benzene
2,5-Dibromo-4,4-bis-(4',4''-dipentylphenyl)-benzene
2,5-Diiodo-4,4-bis-(4',4''-dipentylphenyl)-benzene
2,5-Dimethyl-1,4-bis-(4',4''-dipentylphenyl)-benzene
1-(2-Fluoro-4-pentylphenyl)-2-(4'-pentyldiphenyl)-ethane
1-(3-Fluoro-4-pentylphenyl)-2-(4'-pentyldiphenyl)-ethane
1-(2-Chloro-4-pentylphenyl)-2-(4'-pentyldiphenyl)-ethane
1-(3-Chloro-4-pentylphenyl)-2-(4'-pentyldiphenyl)-ethane
1-(3-Bromo-4-pentylphenyl)-2-(4'-pentyldiphenyl)-ethane
1-(3-Cyano-4-pentylphenyl)-2-(4'-pentyldiphenyl)-ethane
1-(2-Fluoro-4-pentylphenyl)-2-(3-fluor-4'-pentyldiphenyl)-ethane
1-(2-Fluoro-4-pentylphenyl)-2-(3'-fluor-4'-pentyldiphenyl)-ethane
1,4-Bis-[β-(4-pentyl-2-fluorophenyl)-ethyl]-benzene
1,4-Bis-[β-(4-pentyl-3-fluorophenyl)-ethyl]-benzene
1,4-Bis-[β-(4-pentyl-2-chlorophenyl)-ethyl]-benzene
1,4-Bis-[β-(4-pentyl-3-chlorophenyl)-ethyl]-benzene
1,4-Bis-[β-(4-pentyl-2-bromophenyl)-ethyl]-benzene
1,4-Bis-[β-(4-pentyl-3-bromophenyl)-ethyl]-benzene
1,4-Bis-[β-(4-butyloxy-2-fluorophenyl)-ethyl]-benzene
1,4-Bis-[β-(4-butyloxy-3-fluorophenyl)-ethyl]-benzene
1,4-Bis-[β-(4-butyloxy-3-chlorophenyl)-ethyl]-benzene
1-(4'-Pentylphenyl)-2-[2-fluoro-4-(4'-trans-pentylcyclohexyl)phenyl]-ethane
1-(4'-Pentylphenyl)-2-[2-chloro-4-(4'-trans-pentylcyclohexyl)phenyl]-ethane
1-(4'-Pentylphenyl)-2-[2-bromo-4-(4'-trans-pentylcyclohexyl)phenyl]-ethane
1-(4'-Pentylphenyl)-2-[3-fluoro-4-(4'-trans-pentylcyclohexyl)phenyl]-ethane
1-(4'-Pentylphenyl)-2-[3-chloro-4-(4'-trans-pentylcyclohexyl)phenyl]-ethane
1-(4'-Pentylphenyl)-2-[3-bromo-4-(4'-trans-pentylcyclohexyl)phenyl]-ethane
1-(4'-Pentylphenyl)-2-[3-cyano-4-(4'-trans-pentylcyclohexyl)phenyl]-ethane
1-(4'-Pentylphenyl)-2-[3-methyl-4-(4'-trans-pentylcyclohexyl)phenyl]-ethane
1-(4-Butyloxyphenyl)-2-[2-cyano-4-(4'-trans-pentylcyclohexyl)-phenyl]-ethane 1-(4-Butyloxyphenyl)-2-[3-cyano-4-(4'-trans-pentylcyclohexyl)phenyl]-ethane
1-(4-Butyloxy-3-fluorophenyl)-2-[2-[2-fluoro-4-(4'-trans-pentylcyclohexyl)-phenyl]-ethane
1-(4-Butyloxy-3-chlorophenyl)-2-[2-chloro-4-(4'-trans-pentylcyclohexyl)-phenyl]-ethane
1-(4-Butyloxy-3-fluorophenyl)-2-[3-fluoro-4-(4'-trans-pentylcyclohexyl)-phenyl]-ethane
1-(4-Butyloxy-3-chlorophenyl)-2-[3-chloro-4-(4'-trans-pentylcyclohexyl)-phenyl]-ethane
1-(4-Butyloxy-3-bromophenyl)-2-[3-bromo-4-(4'-trans-pentylcyclohexyl)-phenyl]-ethane
1-(4-Butyloxy-3-methylphenyl)-2-[3-methyl-4-(4'-trans-pentylcyclohexyl)-phenyl]-ethane
1-(4-Pentylphenyl)-2-[2-fluoro-4-(4'-trans-pentylcyclohexylmethoxy)-phenyl]-ethane
1-(4-Pentylphenyl)-2-[3-fluoro-4-(4'-trans-pentylcyclohexylmethoxy)-phenyl]-ethane
1-(4-Pentylphenyl)-2-[2-chloro-4-(4'-trans-pentylcyclohexylmethoxy)-phenyl]-ethane
1-(4-Pentylphenyl)-2-[3-chloro-4-(4'-trans-pentylcyclohexylmethoxy)-phenyl]-ethane
1-(4-trans-Pentylcyclohexyl)-2-(2-fluoro-4'-pentyldiphenyl)-ethane
1-(4-trans-Pentylcyclohexyl)-2-(2-chloro-4'-pentyldiphenyl)-ethane
1-(4-trans-Pentylcyclohexyl)-2-(2-bromo-4'-pentyldiphenyl)-ethane
1-(4-trans-Pentylcyclohexyl)-2-(2-iodo-4'-pentyldiphenyl)-ethane
1-(4-trans-Pentylcyclohexyl)-2-(2-methyl-4'-pentyldiphenyl)-ethane
1-(4-trans-Pentylcyclohexyl)-2-(2-cyano-4'-pentyldiphenyl)-ethane
1-(4-trans-Pentylcyclohexyl)-2-(2,2'-difluoro-4'-pentyldiphenyl)-ethane
1-(4-trans-Pentylcyclohexyl)-2-(2,2'-dichloro-4'-pentyldiphenyl)-ethane
1-(4-trans-Pentylcyclohexyl)-2-(3,3'-difluoro-4'-pentyldiphenyl)-ethane
1-(4-trans-Pentylcyclohexyl)-2-(3,3'-dichloro-4'-pentyldiphenyl)-ethane
1-(4-trans-Pentylcyclohexyl)-2-(3-fluoro-4'-pentyldiphenyl)-ethane
1-(4-trans-Pentylcyclohexyl)-2-(3-chloro-4'-pentyldiphenyl)-ethane
1-(4-trans-Pentylcyclohexyl)-2-(3-methyl-4'-pentyldiphenyl)-ethane
1-(4-trans-Pentylcyclohexyl)-2-(3-cyano-4'-pentyldiphenyl)-ethane
1-(4-trans-Pentylcyclohexyl)-2-(3,3'-difluoro-4'-pentyldiphenyl)-ethane
1-(4-trans-Pentylcyclohexyl)-2-(3,3'-dichloro-4'-pentyldiphenyl)-ethane
1-(4-trans-Pentylcyclohexyl)-2-(2'-fluoro-4'-pentyldiphenyl)-ethane
1-(4-trans-Pentylcyclohexyl)-2-(2'-chloro-4'-pentyldiphenyl)-ethane
1-(4-trans-Pentylcyclohexyl)-2-(3'-fluoro-4'-pentyldiphenyl)-ethane
1-(4-trans-Pentylcyclohexyl)-2-(3'-chloro-4'-pentyldiphenyl)-ethane
1-(4-trans-Pentylcyclohexyl)-2-(3'-methyl-4'-pentyldiphenyl)-ethane
1-(4-trans-Pentylcyclohexyl)-2-(3'-cyano-4'-pentyldiphenyl)-ethane
1-(4-trans-Pentylcyclohexyl)-2-(3'-fluoro-4'-butyloxydiphenyl)-ethane
1-(4-trans-Pentylcyclohexyl)-2-(3'-chloro-4'-butyloxydiphenyl)-ethane
1-(4-trans-Pentylcyclohexyl)-2-(3'-bromo-4'-butyloxydiphenyl)-ethane
1-(4-trans-Pentylcyclohexyl)-2-(3'-iodo-4'-butyloxydiphenyl)-ethane
1-(4-trans-Pentylcyclohexyl)-2-(3'-cyano-4'-butyloxydiphenyl)-ethane
1-(4-trans-Pentylcyclohexyl)-2-(3'-methyl-4'-butyloxydiphenyl)-ethane
1-(4-trans-Pentylcyclohexylethyl)-2-(3'-fluoro-4'-butyloxydiphenyl)-ethane
1-(4-trans-Pentylcyclohexylethyl)-2-(3'-chloro-4'-butyloxydiphenyl)-ethane
1-(4-trans-Pentylcyclohexylethyl)-2-(3'-fluoro-4'-propanoyloxydiphenyl)-ethane
5-Propyl-2-(2-fluoro-4-propylphenyl)-pyrimidine
5-Pentyl-2-(2-fluoro-4-propylphenyl)-pyrimidine
5-Pentyl-2-(2-fluoro-4-pentylphenyl)-pyrimidine
5-Heptyl-2-(2-fluoro-4-pentylphenyl)-pyrimidine
5-Pentyl-2-(3-fluoro-4-pentylphenyl)-pyrimidine
5-Heptyl-2-(3-fluoro-4-heptylphenyl)-pyrimidine
5-Pentyl-2-(2-chloro-4-heptylphenyl)-pyrimidine
5-Heptyl-2-(3-chloro-4-heptylphenyl)-pyrimidine
5-Pentyl-2-(3-fluoro-4-butyloxyphenyl)-pyrimidine
5-Heptyl-2-(3-fluoro-4-butyloxyphenyl)-pyrimidine
5-Heptyl-2-(3-fluoro-4-hexyloxyphenyl)-pyrimidine
5-Pentyl-2-(3-chloro-4-butyloxyphenyl)-pyrimidine
5-Heptyl-2-(3-chloro-4-butyloxyphenyl)-pyrimidine
5-Heptyl-2-(3-chloro-4-hexyloxyphenyl)-pyrimidine
5-Pentyl-2-(3-fluoro-4-propanoyloxyphenyl)-pyrimidine
5-Pentyl-2-(3-fluoro-4-pentanoyloxyphenyl)-pyrimidine
5-Heptyl-2-(3-fluoro-4-pentanoyloxyphenyl)-pyrimidine
5-Pentyl-2-(3-chloro-4-pentanoyloxyphenyl)-pyrimidine
5-Heptyl-2-(3-chloro-4-pentanoyloxyphenyl)-pyrimidine
2-Propyl-5-(2-fluoro-4-propylphenyl)-pyrimidine
2-Pentyl-5-(2-fluoro-4-propylphenyl)-pyrimidine
2-Pentyl-5-(2-fluoro-4-pentylphenyl)-pyrimidine
2-Heptyl-5-(2-fluoro-4-pentylphenyl)-pyrimidine
2-Pentyl-5-(3-fluoro-4-pentylphenyl)-pyrimidine
2-Heptyl-5-(3-fluoro-4-heptylphenyl)-pyrimidine
2-Pentyl-5-(2-chloro-4-heptylphenyl)-pyrimidine
2-Heptyl-5-(3-chloro-4-heptylphenyl)-pyrimidine
2-Pentyl-5-(3-fluoro-4-butyloxyphenyl)-pyrimidine
2-Heptyl-5-(3-fluoro-4-butyloxyphenyl)-pyrimidine
2-Heptyl-5-(3-fluoro-4-hexyloxyphenyl)-pyridimine
2-Pentyl-5-(3-chloro-4-butyloxyphenyl)-pyrimidine
2-Heptyl-5-(3-chloro-4-butyloxyphenyl)-pyrimidine
2-Heptyl-5-(3-chloro-4-hexyloxyphenyl)-pyrimidine
2-Pentyl-5-(3-fluoro-4-propanoyloxyphenyl)-pyrimidine
2-Pentyl-5-(3-fluoro-4-pentanoyloxyphenyl)-pyrimidine
2-Heptyl-5-(3-fluoro-4-pentanoyloxyphenyl)-pyrimidine
2-Pentyl-5-(3-chloro-4-pentanoyloxyphenyl)-pyrimidine
2-Heptyl-5-(3-chloro-4-pentanoyloxyphenyl)-pyrimidine
1-(5-Pentyl-2-pyrimidinyl)-2-(2-fluoro-4-pentylphenyl)-ethane
1-(5-Pentyl-2-pyrimidinyl)-2-(3-fluoro-4-pentylphenyl)-ethane
1-(5-Pentyl-2-pyrimidinyl)-2-(2-chloro-4-pentylphenyl)-ethane 1-(5-Pentyl-2-pyrimidinyl)-2-(3-chloro-4-pentylphenyl)-ethane
1-(5-Pentyl-2-pyrimidinyl)-2-(3-fluoro-4-butyloxyphenyl)-ethane
1-(5-Pentyl-2-pyrimidinyl)-2-(3-chloro-4-butyloxyphenyl)-ethane
1-(5-Pentyl-2-pyrimidinyl)-2-(3-fluoro-4-propanoyloxyphenyl)-ethane
1-(5-Pentyl-2-pyrimidinyl)-2-(3-chloro-4-propanoyloxyphenyl)-ethane
5-(4-Pentylphenyl)-2-(2-fluoro-4-pentylphenyl)-pyrimidine
5-(4-Pentylphenyl)-2-(3-fluoro-4-pentylphenyl)-pyrimidine
5-(4-Pentylphenyl)-2-(3-chloro-4-pentylphenyl)-pyrimidine
5-(4-Pentylphenyl)-2-(3-fluoro-4-butyloxyphenyl)-pyrimidine
5-(4-Pentylphenyl)-2-(3-chloro-4-butyloxyphenyl)-pyrimidine
5-(4-Pentylphenyl)-2-(3-fluoro-4-propanoyloxyphenyl)-pyrimidine
2,5-Bis-(2-fluoro-4-pentylphenyl)-pyrimidine
2,5-Bis-(3-fluoro-4-pentylphenyl)-pyrimidine
2,5-Bis-(3-chloro-4-pentylphenyl)-pyrimidine
2,5-Bis-(3-fluoro-4-butyloxyphenyl)-pyrimidine
2,5-Bis-(3-chloro-4-butyloxyphenyl)-pyrimidine
2,5-Bis-(3-fluoro-4-propanoyloxyphenyl)-pyrimidine
2,5-Bis-(3-chloro-4-propanoyloxyphenyl)-pyrimidine
1-(2-Pentyl-5-pyrimidinyl)-2-(2-fluoro-4-pentylphenyl)-ethane
1-(2-Pentyl-5-pyrimidinyl)-2-(3-fluoro-4-pentylphenyl)-ethane
1-(2-Pentyl-5-pyrimidinyl)-2-(2-chloro-4-pentylphenyl)-ethane
1-(2-Pentyl-5-pyrimidinyl)-2-(3-chloro-4-pentylphenyl)-ethane
1-(2-Pentyl-5-pyrimidinyl)-2-(3-fluoro-4-butyloxyphenyl)ethane
1-(2-Pentyl-5-pyrimidinyl)-2-(3-chloro-4-butyloxyphenyl)ethane
1-(2-Pentyl-5-pyrimidinyl)-2-(3-fluoro-4-propanoyloxyphenyl)ethane
1-(2-Pentyl-5-pyrimidinyl)-2-(3-chloro-4-propanoyloxyphenyl)ethane
2-(4-Pentylphenyl)-5-(2-fluoro-4-pentylphenyl)-pyrimidine
2-(4-Pentylphenyl)-5-(3-fluoro-4-pentylphenyl)-pyrimidine
2-(4-Pentylphenyl)-5-(3-chloro-4-pentylphenyl)-pyrimidine
2-(4-Pentylphenyl)-5-(3-fluoro-4-butyloxyphenyl)-pyrimidine
2-(4-Pentylphenyl)-5-(3-chloro-4-butyloxyphenyl)-pyrimidine
2-(4-Pentylphenyl)-5-(3-fluoro-4-propanoyloxyphenyl)-pyrimidine
2-Pentyl-5-(2-fluoro-4'-pentyldiphenyl)-pyrimidine
2-Pentyl-5-(2-chloro-4'-pentyldiphenyl)-pyrimidine
2-Pentyl-5-(2-bromo-4'-pentyldiphenyl)-pyrimidine
2-Pentyl-5-(3-fluoro-4'-pentyldiphenyl)-pyrimidine
2-Pentyl-5-(3-chloro-4'-pentyldiphenyl)-pyrimidine
2-Pentyl-5-(3-bromo-4'-pentyldiphenyl)-pyrimidine
2-Pentyl-5-(3-cyano-4'-pentyldiphenyl)-pyrimidine
2-Pentyl-5-(3'-fluoro-4'-butyloxydiphenyl)-pyrimidine
2-Pentyl-5-(3'-chloro-4'-butyloxydiphenyl)-pyrimidine
2-Pentyl-5-(3'-bromo-4'-butyloxydiphenyl)-pyrimidine
2-Pentyl-5-(3'-cyano-4'-butyloxydiphenyl)-pyrimidine
2-Pentyl-5-(3'-methyl-4'-butyloxydiphenyl)-pyrimidine
2-Pentyl-5-(3'-chloro-4'-propanoyloxydiphenyl)-pyrimidine
5-Pentyl-2-[2-fluoro-4-(4-pentylphenylethyl)-phenyl]-pyrimidine
5-Pentyl-2-[2-chloro-4-(4-pentylphenylethyl)-phenyl]-pyrimidine
5-Pentyl-2-[2-bromo-4-(4-pentylphenylethyl)-phenyl]-pyrimidine
5-Pentyl-2-[2-cyano-4-(4-pentylphenylethyl)-phenyl]-pyrimidine
5-Pentyl-2-(2-fluoro-4'-pentyldiphenyl)-pyrimidine
5-Pentyl-2-(2-chloro-4'-pentyldiphenyl)-pyrimidine
5-Pentyl-2-(2-bromo-4'-pentyldiphenyl)-pyrimidine
5-Pentyl-2-(3-fluoro-4'-pentyldiphenyl)-pyrimidine
5-Pentyl-2-(3-chloro-4'-pentyldiphenyl)-pyrimidine
5-Pentyl-2-(3-bromo-4'-pentyldiphenyl)-pyrimidine
5-Pentyl-2-(3-cyano-4'-pentyldiphenyl)-pyrimidine
5-Pentyl-2-(3'-fluoro-4'-butyloxydiphenyl)-pyrimidine
5-Pentyl-2-(3'-chloro-4'-butyloxydiphenyl)-pyrimidine
5-Pentyl-2-(3'-bromo-4'-butyloxydiphenyl)-pyrimidine
5-Pentyl-2-(3'-cyano-4'-butyloxydiphenyl)-pyrimidine
5-Pentyl-2-(3'-methyl-4'-butyloxydiphenyl)-pyrimidine
5-Pentyl-2-(3'-chloro-4'-propanoyloxydiphenyl)-pyrimidine
2-Pentyl-5-[2-fluoro-4-pentylphenylethyl)-phenyl]-pyrimidine
2-Pentyl-5-[2-chloro-4-pentylphenylethyl)-phenyl]-pyrimidine
2-Pentyl-5-[2-bromo-4-(4-pentylphenylethyl)-phenyl]-pyrimidine
2-Pentyl-5-[2-cyano-4-pentylphenylethyl)-phenyl]-pyrimidine
5-(trans-4-Pentylcyclohexyl)-2-(2-fluoro-4-pentylphenyl)-pyrimidine
5-(trans-4-Pentylcyclohexyl)-2-(2-chloro-4-pentylphenyl)-pyrimidine
5-(trans-4-Pentylcyclohexyl)-2-(2-bromo-4-pentylphenyl)-pyrimidine
5-(trans-4-Pentylcyclohexyl)-2-(2-cyano-4-pentylphenyl)-pyrimidine
5-(trans-4-Pentylcyclohexyl)-2-(2-methyl-4-pentylphenyl)-pyrimidine
5-(trans-4-Pentylcyclohexyl)-2-(3-fluoro-4-pentylphenyl)-pyrimidine
5-(trans-4-Pentylcyclohexyl)-2-(3-chloro-4-pentylphenyl)-pyrimidine
5-(trans-4-Pentylcyclohexyl)-2-(3-bromo-4-pentylphenyl)-pyrimidine
5-(trans-4-Pentylcyclohexyl)-2-(3-cyano-4-pentylphenyl)-pyrimidine
5-(trans-4-Pentylcyclohexyl)-2-(3-methyl-4-pentylphenyl)-pyrimidine
5-(trans-4-Pentylcyclohexyl)-2-(3-fluoro-4-butyloxyphenyl)-pyrimidine
5-(trans-4-Pentylcyclohexyl)-2-(3-chloro4-butyloxyphenyl)-pyrimidine
5-(trans-4-Pentylcyclohexyl)-2-(3-bromo-4-butyloxyphenyl)-pyrimidine
5-(trans-4-Pentylcyclohexyl)-2-(3-cyano-4-butyloxyphenyl)-pyrimidine
5-(trans-4-Pentylcyclohexyl)-2-(3-fluoro-4-propanoyloxyphenyl)-pyrimidine
5-(trans-4-Pentylcyclohexyl)-2-(3-chloro-4-propanoyloxyphenyl)-pyrimidine
5-(trans-4-Pentylcyclohexyl)-2-(3-bromo-4-propanoyloxyphenyl)-pyrimidine 5-(trans-4-Pentylcyclohexyl)-2-(3-cyano-4-propanoyloxyphenyl)pyrimidine
2-(trans-4-Pentylcyclohexyl)-5-(2-fluoro-4-pentylphenyl)-pyrimidine
2-(trans-4-Pentylcyclohexyl)-5-(2-chloro-4-pentylphenyl)-pyrimidine
2-(trans-4-Pentylcyclohexyl)-5-(2-bromo-4-pentylphenyl)-pyrimidine
2-(trans-4-Pentylcyclohexyl)-5-(2-cyano-4-pentylphenyl)-pyrimidine
2-(trans-4-Pentylcyclohexyl)-5-(2-methyl-4-pentylphenyl)-pyrimidine
2-(trans-4-Pentylcyclohexyl)-5-(3-fluoro-4-pentylphenyl)-pyrimidine
2-(trans-4-Pentylcyclohexyl)-5-(3-chloro-4-pentylphenyl)-pyrimidine
2-(trans-4-Pentylcyclohexyl)-5-(3-bromo-4-pentylphenyl)-pyrimidine
2-(trans-4-Pentylcyclohexyl)-5-(3-cyano-4-pentylphenyl)-pyrimidine
2-(trans-4-Pentylcyclohexyl)-5-(3-methyl-4-pentylphenyl)-pyrimidine
2-(trans-4-Pentylcyclohexyl)-5-(3-fluoro-4-butyloxyphenyl)-pyrimidine
2-(trans-4-Pentylcyclohexyl)-5-(3-chloro-4-butyloxyphenyl)-pyrimidine
2-(trans-4-Pentylcyclohexyl)-5-(3-bromo-4-butyloxyphenyl)-pyrimidine
2-(trans-4-Pentylcyclohexyl)-5-(3-cyano-4-butyloxyphenyl)-pyrimidine
2-(trans-4-Pentylcyclohexyl)-5-(3-fluoro-4-propanoyloxyphenyl)-pyrimidine
2-(trans-4-Pentylcyclohexyl)-5-(3-chloro-4-propanoyloxyphenyl)-pyrimidine
2-(trans-4-Pentylcyclohexyl)-5-(3-bromo-4-propanoyloxyphenyl)-pyrimidine
2-(trans-4-Pentylcyclohexyl)-5-(3-cyano-4-propanoyloxyphenyl)-pyrimidine
5-(trans-4-Pentylcyclohexylethyl)-2-(2-fluoro-4-pentylphenyl)-pyrimidine
5-(trans-4-Pentylcyclohexylethyl)-2-(2-chloro-4-pentylphenyl)-pyrimidine
5-(trans-4-Pentylcyclohexylethyl)-2-(2-bromo-4-pentylphenyl)-pyrimidine
5-(trans-4-Pentylcyclohexylethyl)-2-(2-cyano-4-pentylphenyl)-pyrimidine
5-(trans-4-Pentylcyclohexylethyl)-2-(2-methyl-4-pentylphenyl)-pyrimidine
5-(trans-4-Pentylcyclohexylethyl)-2-(3-fluoro-4-pentylphenyl)-pyrimidine
5-(trans-4-Pentylcyclohexylethyl)-2-(3-chloro-4-pentylphenyl)-pyrimidine
5-(trans-4-Pentylcyclohexylethyl)-2-(3-bromo-4-pentylphenyl)-pyrimidine
5-(trans-4-Pentylcyclohexylethyl)-2-(3-cyano-4-pentylphenyl)-pyrimidine
5-(trans-4-Pentylcyclohexylethyl)-2-(3-methyl-4-pentylphenyl)-pyrimidine
5-(trans-4-Pentylcyclohexylethyl)-2-(3-fluoro-4-butyloxyphenyl)-pyrimidine
5-(trans-4-Pentylcyclohexylethyl)-2-(3-chloro-4-butyloxyphenyl)-pyrimidine
5-(trans-4-Pentylcyclohexylethyl)-2-(3-bromo-4-butyloxyphenyl)-pyrimidine
5-(trans-4-Pentylcyclohexylethyl)-2-(3-cyano-4-butyloxyphenyl)-pyrimidine
5-(trans-4-Pentylcyclohexylethyl)-2-(3-fluoro-4-propanoyloxyphenyl)-pyrimidine
5-(trans-4-Pentylcyclohexylethyl)-2-(3-chloro-4-propanoyloxyphenyl)-pyrimidine
5-(trans-4-Pentylcyclohexylethyl)-2-(3-bromo-4-propanoyloxyphenyl)-pyrimidine
5-(trans-4-Pentylcyclohexylethyl)-2-(3-cyano-4-propanoyloxyphenyl)-pyrimidine
2-(trans-4-Pentylcyclohexylethyl)-5-(2-fluoro-4pentylphenyl)-pyrimidine
2-(trans-4-Pentylcyclohexylethyl)-5-(2-chloro-4-pentylphenyl)-pyrimidine
2-(trans-4-Pentylcyclohexylethyl)-5-(2-bromo-4-pentylphenyl)-pyrimidine
2-(trans-4-Pentylcyclohexylethyl)-5-(2-cyano-4-pentylphenyl)-pyrimidine
2-(trans-4-Pentylcyclohexylethyl)-5-(2-methyl-4-pentylphenyl)-pyrimidine
2-(trans-4-Pentylcyclohexylethyl)-5-(3-fluoro-4-pentylphenyl)-pyrimidine
2-(trans-4-Pentylcyclohexylethyl)-5-(3-chloro-4-pentylphenyl)-pyrimidine
2-(trans-4-Pentylcyclohexylethyl)-5-(3-bromo-4-pentylphenyl)-pyrimidine
2-(trans-4-Pentylcyclohexylethyl)-5-(3-cyano-4-pentylphenyl)-pyrimidine
2-(trans-4-Pentylcyclohexylethyl)-5-(3-methyl-4-pentylphenyl)-pyrimidine
2-(trans-4-Pentylcyclohexylethyl)-5-(3-fluoro-4-butyloxyphenyl)-pyrimidine
2-(trans-4-Pentylcyclohexylethyl)-5-(3-chloro-4-butyloxyphenyl)-pyrimidine
2-(trans-4-Pentylcyclohexylethyl)-5-(3-bromo-4-butyloxyphenyl)-pyrimidine
2-(trans-4-Pentylcyclohexylethyl)-5-(3-cyano butyloxyphenyl)-pyrimidine
2-(trans-4-Pentylcyclohexylethyl)-5-(3-fluoro-4propanoyloxyphenyl)-pyrimidine
2-(trans-4-Pentylcyclohexylethyl)-5-(3-chloro-4-propanoyloxyphenyl)-pyrimidine
2-(trans-4-Pentylcyclohexylethyl)-5-(3-bromo-4-propanoyloxyphenyl)-pyrimidine
2-(trans-4-Pentylcyclohexylethyl)-5-(3-cyano-4-propanoyloxyphenyl)-pyrimidine
5-(trans-4-Pentylcyclohexylmethoxy)-2-(2-fluoro-4-pentylphenyl)-pyrimidine
5-(trans-4-Pentylcyclohexylmethoxy)-2-(2-chloro-4-pentylphenyl)-pyrimidine
5-(trans-4-Pentylcyclohexylmethoxy)-2-(2-bromo-4-pentylphenyl)-pyrimidine
5-(trans-4-Pentylcyclohexylmethoxy)-2-(2-cyano-4-pentylphenyl)-pyrimidine
5-(trans-4-Pentylcyclohexylmethoxy)-2-(2-methyl-4-pentylphenyl)-pyrimidine
5-(trans-4-Pentylcyclohexylmethoxy)-2-(3-fluoro-4-pentylphenyl)-pyrimidine
5-(trans-4-Pentylcyclohexylmethoxy)-2-(3-chloro-4-pentylphenyl)-pyrimidine
5-(trans-4-Pentylcyclohexylmethoxy)-2-(3-bromo-4-pentylphenyl)-pyrimidine
5-(trans-4-Pentylcyclohexylmethoxy)-2-(3-cyano-4-pentylphenyl)-pyrimidine
5-(trans-4-Pentylcyclohexylmethoxy)-2-(3-methyl-4-pentylphenyl)-pyrimidine
5-(trans-4-Pentylcyclohexylmethoxy)-2-(3-fluoro-4-butyloxyphenyl)-pyrimidine
5-(trans-4-Pentylcyclohexylmethoxy)-2-(3-chloro-4-butyloxyphenyl)-pyrimidine
5-(trans-4-Pentylcyclohexylmethoxy)-2-(3-bromo-4-butyloxyphenyl)-pyrimidine 5-(trans-4-Pentylcyclohexylmethoxy)-2-(3-cyano-4-butyloxyphenyl)-pyrimidine
5-(trans-4-Pentylcyclohexylmethoxy)-2-(3-fluoro-4-propanoyloxyphenyl)-pyrimidine
5-(trans-4-Pentylcyclohexylmethoxy)-2-(3-chloro-4-propanoyloxyphenyl)-pyrimidine
5-(trans-4-Pentylcyclohexylmethoxy)-2-(3-bromo-4-propanoyloxyphenyl)-pyrimidine
5-(trans-4-Pentylcyclohexylmethoxy)-2-(3-cyano-4-propanoyloxyphenyl)-pyrimidine
2-(trans-4-Pentylcyclohexylmethoxy)-5-(2-fluoro-4-pentylphenyl)-pyrimidine
2-(trans-4-Pentylcyclohexylmethoxy)-5-(2-chloro-4-pentylphenyl)-pyrimidine
2-(trans-4-Pentylcyclohexylmethoxy)-5-(2-bromo-4-pentylphenyl)-pyrimidine
2-(trans-4-Pentylcyclohexylmethoxy)-5-(2-cyano-4-pentylphenyl)-pyrimidine
2-(trans-4-Pentylcyclohexylmethoxy)-5-(2-methyl-4-pentylphenyl)-pyrimidine
2-(trans-4-Pentylcyclohexylmethoxy)-5-(3-fluoro-4-pentylphenyl)-pyrimidine
2-(trans-4-Pentylcyclohexylmethoxy)-5-(3-chloro-4-pentylphenyl)-pyrimidine
2-(trans-4-Pentylcyclohexylmethoxy)-5-(3-bromo-4-pentylphenyl)-pyrimidine
2-(trans-4-Pentylcyclohexylmethoxy)-5-(3-cyano-4-pentylphenyl)-pyrimidine
2-(trans-4-Pentylcyclohexylmethoxy)-5-(3-fluoro-4-butyloxyphenyl)-pyrimidine
2-(trans-4-Pentylcyclohexylmethoxy)-5-(3-chloro-4-butyloxyphenyl)-pyrimidine
2-(trans-4-Pentylcyclohexylmethoxy)-5-(3-bromo-4-butyloxyphenyl)-pyrimidine
2-(trans-4-Pentylcyclohexylmethoxy)-5-(3-cyano-4-butyloxyphenyl)-pyrimidine
2-(trans-4-Pentylcyclohexylmethoxy)-5-(3-fluoro-4-propanoyloxyphenyl)-pyrimidine
2-(trans-4-Pentylcyclohexylmethoxy)-5-(3-chloro-4-propanoyloxyphenyl)-pyrimidine
2-(trans-4-Pentylcyclohexylmethoxy)-5-(3-bromo-4-propanoyloxyphenyl)-pyrimidine
2-(trans-4-Pentylcyclohexylmethoxy)-5-(3-cyano-4-propanoyloxyphenyl)-pyrimidine
2-Chloro-4-propyl-4'-(4-propyphenyl)terphenyl
2-Cloro-4-pentyl-4'-(4-propylphenyl)terphenyl
2-Cloro-4-pentyl-4'-(4-pentylphenyl)terphenyl
3-Cloro-4-pentyl-4'-(4-pentylphenyl)terphenyl
2-Bromo-4-pentyl-4'-(4-pentylphenyl)terphenyl
3-Bromo-4-pentyl-4'-(4-pentylphenyl)terphenyl
2-Methyl-4-pentyl-4'-(4-pentylphenyl)terphenyl
3-Methyl-4-pentyl-4'-(4-pentylphenyl)terphenyl
2-Bromo-4-butyloxy-4'-(4-pentylphenyl)terphenyl
2-Methyl-4-butyloxy-4'-(4-pentylphenyl)terphenyl
2-Cyano-4-butyloxy-4'-(4-pentylphenyl)terphenyl
2-Chloro-1,4-bis(4',4''-dipentylphenyl)diphenyl
2-Bromo-1,4-bis(4',4''-dipentylphenyl)diphenyl
2-Cyano-1,4-bis(4',4''-dipentylphenyl)diphenyl
2-Methyl-1,4-bis(4',4''-dipentylphenyl)diphenyl
1,4-Bis(3-chloro-4-pentylphenyl)diphenyl
1,4-Bis(3-bromo-4-pentylphenyl)diphenyl
1,4-Bis(3-methyl-4-pentylphenyl)diphenyl
1-(2-Chloro-4-pentyldiphenyl)-2-(4'-pentyldiphenyl)-ethane
1-(2-Bromo-4-pentyldiphenyl)-2-(4'-pentyldiphenyl)-ethane
1-(2-Cyano-4-pentyldiphenyl)-2-(4'-pentyldiphenyl)-ethane
1-(2-Methyl-4-pentyldiphenyl)-2-(4'-pentyldiphenyl)-ethane
1-(4'-Pentyldiphenyl)-2-[2-bromo-4'-trans-pentylcyclohexyl) phenyl]-ethane
1-(4-Butyloxy-3-methyldiphenyl)-2-[3-methyl-4-(4'-transpentylcyclohexyl)phenyl]-ethane
1-(4-Pentyldiphenyl)-2-[2-bromo-4(4'-trans-pentylcyclohexylmethoxy)-phenyl]-ethane
5-(4-Pentyldiphenyl)-2-(2-chloro-4-pentylphenyl)-pyrimidine
5-(4-Pentyldiphenyl)-2-(2-bromo-4-pentylphenyl)-pyrimidine
5-(4-Pentyldiphenyl)-2-(2-methyl-4-pentylphenyl)-pyrimidine
5-(4-Pentyldiphenyl)-2-(2-iodo-4-pentylphenyl)-pyrimidine
5-(3-Chlor-4-pentyldiphenyl)-2-(2-chloro-4-pentyldiphenyl)-pyrimidine
2-(4-Pentylphenyl)-5-(3'-bromo-4'-butyloxydiphenyl)-pyrimidine
2-(4-Pentylphenyl)-5-(3'-iodo-4'-butyloxydiphenyl)-pyrimidine
2-(4-Pentylphenyl)-5-(3'-methyl-4'-butyloxydiphenyl-pyrimidine
5-(4-Pentylphenyl)-2-[2-bromo-4-(4'-pentylphenyl-ethyl)phenyl]pyrimidine
5-(trans-4-Pentylcyclohexyl)-2-(2-bromo-4-pentyldiphenyl)-pyrimidine
5-(trans-4-Pentylcyclohexyl)-2-(2-methyl-4-pentyldiphenyl)-pyrimidine
5-(trans-4-Pentylcyclohexyl)-2-(2-cyano-4-pentyldiphenyl)-pyrimidine
5-(trans-4-Pentylcyclohexyl)-2-(2-iodo-4-pentyldiphenyl)-pyrimidine
5-(trans-4-Pentylcyclohexyl)-2-(3-chloro-4-butyloxydiphenyl)-pyrimidine
5-(trans-4-Pentylcyclohexyl)-2-(3-bromo-4-butyloxydiphenyl)-pyrimidine
5-(trans-4-Pentylcyolohexyl)-2-(3-cyano-4-butyloxydiphenyl)-pyrimidine
5-(trans-4-Pentyloyclohexyl)-2-(3-methyl-4-butyloxydiphenyl)-pyrimidine
5-(trans-4-Pentylcyclohexyl)-2-(3-bromo-4-pentyldiphenyl)-pyrimidine
5-(trans-4-Pentylcyclohexyl)-2-(3-cyano-4-pentyldiphenyl)-pyrimidine
5-(trans-4-Pentylcyclohexyl)-2-(3-methyl-4-pentyldiphenyl)-pyrimidine
5-(trans-4-Pentylcyclohexyl-ethyl)-2-(2-chloro-4-pentyldiphenyl)-pyrimidine
5-(trans-4-Pentylcyclohexyl-ethyl)-2-(2-bromo-4-pentyldiphenyl)-pyrimidine
5-(trans-4-Pentylcyclohexyl-ethyl)-2-(2-cyano-4-pentyldiphenyl)-pyrimidine
5-(trans-4-Pentylcyclohexyl-ethyl)-2-(2-methyl-4-pentyldiphenyl)-pyrimidine
2-Cyano-4,4'-dipentyl-diphenyl
3-Cyano-4,4'-dipentyl-diphenyl
3-Cyano-4-butyloxy-4'-pentyldiphenyl
2-Cyano-4-(4-trans-pentylcyclohexyl)-butyloxybenzene
1-(2-Cyano-4-pentylphenyl)-2-(4-pentylphenyl)-ethane
2,3-Dicyano-1,4-bis(4',4''-dipentylphenyl)-benzene
1-Butyloxy-2,3-dicyano-4-(4'-pentylbiphenylyl)-benzene
1-Pentyl-2,3-dicyano-4-(4'-pentylbiphenylyl)-benzene
1-(2,3-Dicyano-4-pentylphenyl)-2-(4'-pentylbiphenylyl)-ethane 1-(2,3-Dicyano-4-butyloxyphenyl)-2-(4'-pentylbiphenylyl)-ethane
1-(2,3-Dicyano-4-butyloxyphenyl)-2-[4-(4'-trans-pentylcyclohexyl)-phenyl]-ethane
1-(2,3-Dicyano-4-pentylphenyl)-2-[4-(4'-trans-pentylcyclohexyl)phenyl]-ethane
1-(4-Pentylphenyl)-2-[4-(4'-trans-pentylcyclohexyl)-2,3-dicyanophenyl]-ethane
1-(2,3-Dicyano-4-pentylphenyl)-2-(4,4'-trans,trans-pentylbicyclohexyl)-ethane
1-(2,3-Dicyano-4-butyloxyphenyl)-2-(4,4'-trans,trans-pentylbicyclohexyl)-ethane
2-Methyl-1-pentyl-4-(4-trans-pentylcyclohexyl)-benzene
3-Methyl-1-pentyl-4-(4-trans-pentylcyclohexyl)-benzene
2-Methyl-1-nonyl-4-(4-trans-pentylcyclohexyl)-benzene
3-Methyl-1-nonyl-4-(4-trans-pentylcyclohexyl)-benzene
2-Methyl-1-nonyl-4-(4-trans-nonylcyclohexyl)-benzene
3-Methyl-1-nonyl-4-(4-trans-nonylcyclohexyl)-benzene
2-Methyl-4-(4-trans-nonylcyclohexyl)-1-pentyl-benzene
3-Methyl-4-(4-trans-nonylcyclohexyl)-1-pentyl-benzene
1-Butoxy-2-methyl-4-(4-trans-pentylcyclohexyl)-benzene
1-Butoxy-3-methyl-4-(4-trans-pentylcyclohexyl)-benzene
1-Butoxy-2-methyl-4-(4-trans-nonylcyclohexyl)-benzene
1-Butoxy-3-methyl-4-(4-trans-nonylcyclohexyl)-benzene
2-Methyl-4-(4-trans-nonylcyclohexyl)-1-octyloxy-benzene
3-Methyl-4-(4-trans-nonylcyclohexyl)-1-octyloxy-benzene
2-Methyl-1-octyloxy-4-(4-trans-pentylcyclohexyl)-benzene
3-Methyl-1-octyloxy-4-(4-trans-pentylcyclohexyl)-benzene
2-Methyl-4-(4-trans-pentylcyclohexyl)-phenyl-butanoate
3-Methyl-4-(4-trans-pentylcyclohexyl)-phenyl-butanoate
2-Methyl-4-(4-trans-nonylcyclohexyl)-phenyl-butanoate
3-Methyl-4-(4-trans-nonylcyclohexyl)-phenyl-butanoate
2-Methyl-4-(4-trans-pentylcyclohexyl)-phenyl-octanoate
3-Methyl-4-(4-trans-pentylcyclohexyl)-phenyl-octanoate
2-Methyl-4-(4-trans-nonylcyclohexyl)-phenyl-octanoate
3-Methyl-4-(4-trans-nonylcyclohexyl)-phenyl-octanoate
N-Butyl-2-methyl-4-(4-trans-pentylcyclohexyl)-aniline
N-Butyl-3-methyl-4-(4-trans-pentylcyclohexyl)-aniline
N-Butyl-2-methyl-4-(4-trans-nonylcyclohexyl)-aniline
N-Butyl-3-methyl-4-(4-trans-nonylcyclohexyl)-aniline
N-Octyl-2-methyl-4-(4-trans-pentylcyclohexyl)-aniline
N-Octyl-3-methyl-4-(4-trans-pentylcyclohexyl)-aniline
N-Octyl-2-methyl-4-(4-trans-nonylcyclohexyl)-aniline
N-Octyl-3-methyl-4-(4-trans-nonylcyclohexyl)-aniline
1-(4-trans-Pentylcyclohexyl)-2-(2-methyl-4-pentylphenyl)-ethane
1-(4-trans-Pentylcyclohexyl)-2-(3-methyl-4-pentylphenyl)-ethane
1-(4-trans-Pentylcyclohexyl)-2-(2-methyl-4-nonylphenyl)-ethane
1-(4-trans-Pentylcyclohexyl)-2-(3-methyl-4-nonylphenyl)-ethane
1-(4-trans-Nonylcyclohexyl)-2-(2-methyl-4-pentylphenyl)-ethane
1-(4-trans-Nonylcyclohexyl)-2-(3-methyl-4-pentylphenyl)-ethane
1-(4-trans-Nonylcyclohexyl)-2-(2-methyl-4-nonylphenyl)-ethane
1-(4-trans-Nonylcyclohexyl)-2-(3-methyl-4-nonylphenyl)-ethane
1-(4-trans-Pentylcyclohexyl)-2-(4-butoxy-2-methylphenyl)-ethane
1-(4-trans-Pentylcyclohexyl)-2-(4-butoxy-3-methylphenyl)-ethane
1-(4-trans-Pentylcyclohexyl)-2-(2-methyl-4-octyloxyphenyl)-ethane
1-(4-trans-Pentylcyclohexyl)-2-(3-methyl-4-octyloxyphenyl)-ethane
1-(4-trans-Nonylcyclohexyl)-2-(4-butoxy-2-methylphenyl)-ethane
1-(4-trans-Nonylcyclohexyl)-2-(4-butoxy-3-methylphenyl)-ethane
1-(4-trans-Nonylcyclohexyl)-2-(2-methyl-4-octyloxyphenyl)-ethane
1-(4-trans-Nonylcyclohexyl)-2-(3-methyl-4-octyloxyphenyl)-ethane
1-(4-trans-Pentylcyclohexyl)-2-(4-N-butylamino-2-methylphenyl)-ethane
1-(4-trans-Pentylcyclohexyl)-2-(4-N-butylamino-3-methylphenyl)-ethane
1-(4-trans-Pentylcyclohexyl)-2-(2-methyl-4-N-octylaminophenyl)-ethane
1-(4-trans-Pentylcyclohexyl)-2-(3-methyl-4-N-octylaminophenyl)-ethane
1-(4-trans-Nonylcyclohexyl)-2-(4-N-butylamino-2-methylphenyl)-ethane
1-(4-trans-Nonylcyclohexyl)-2-(4-N-butylamino-3-methylphenyl)-ethane
1-(4-trans-Nonylcyclohexyl)-2-(2-methyl-4-N-octylaminophenyl)-ethane
1-(4-trans-Nonylcyclohexyl)-2-(3-methyl-4-N-octylaminophenyl)-ethane
1-(4-trans-Pentylcyclohexyl)-2-(4-butanoyloxy-2-methylphenyl)-ethane
1-(4-trans-Pentylcyclohexyl)-2-(4-butanoyloxy-3-methylphenyl)-ethane
1-(4-trans-Pentylcyclohexyl)-2-(2-methyl-4-octanoyloxyphenyl)-ethane
1-(4-trans-Pentylcyclohexyl)-2-(3-methyl-4-octanoyloxyphenyl)-ethane
1-(4-trans-Nonylcyclohexyl)-2-(4-butanoyloxy-2-methylphenyl)-ethane
1-(4-trans-Nonylcyclohexyl)-2-(4-butanoyloxy-3-methylphenyl)-ethane
1-(4-trans-Nonylcyclohexyl)-2-(2-methyl-4-octanoyloxyphenyl)-ethane
1-(4-trans-Nonylcyclohexyl)-2-(3-methyl-4-octanoyloxyphenyl)-ethane
(4-trans-Pentylcyclohexylmethyl)-(2-methyl-4-pentylphenyl)-ether
(4-trans-Pentylcyclohexylmethyl)-(3-methyl-4-pentylphenyl)-ether
(4-trans-Pentylcyclohexylmethyl)-(4-butoxy-2-methylphenyl)-ether
(4-trans-Pentylcyclohexylmethyl)-(4-butoxy-3-methylphenyl)-ether
(4-trans-Pentylcyclohexylmethyl)-(4-N-butylamino-2-methylphenyl)-ether (4-trans-Pentylcyclohexylmethyl)-(4-N-butylamino-3-methylphenyl)-ether
(4-trans-Pentylcyclohexylmethyl)-(2-methyl-4-octanoyloxyphenyl)-ether
(4-trans-Pentylcyclohexylmethyl)-(3-methyl-4-octanoyloxyphenyl)-ether
4-(4-trans-Pentylcyclohexyl)-2-methyl-4'-pentyl-biphenyl
4-(4-trans-Pentylcyclohexyl)-3-methyl-4'-pentyl-biphenyl
4-(4-trans-Pentylcyclohexyl)-2-methyl-4'-octanoyloxybiphenyl
4-(4-trans-Pentylcyclohexyl)-3-methyl-4'-octanoyloxybiphenyl
4'-Butoxy-4-(4-trans-pentylcyclohexyl)-2-methylbiphenyl
4'-Butoxy-4-(4-trans-pentylcyclohexyl)-3-methylbiphenyl
4'-N-Butylamino-4-(4-trans-pentylcyclohexyl)-2-methyl-biphenyl
4'-N-Butylamino-4-(4-trans-pentylcyclohexyl)-3-methyl-biphenyl
4-(4-trans-Pentylcyclohexyl)-3,3'-dimethyl-4'-pentylbiphenyl
4-(4-trans-Pentylcyclohexyl)-3,3'-dimethyl-4'-octanoyloxybiphenyl
4'-N-Butylamino-4-(4-trans-pentylcyclohexyl)-3,3'-dimethylbiphenyl
4'-Butoxy-4-(4-trans-pentylcyclohexyl)-3,3'-dimethylbiphenyl
1-(4-(4-trans-Pentylcyclohexyl)-2-methylphenyl)-2-(4-pentylphenyl)-ethane
1-(4-(4-trans-Pentylcyclohexyl)-3-methylphenyl)-2-(4-pentylphenyl)-ethane
1-(4-(4-trans-Pentylcyclohexyl)-2-methylphenyl)-2-(4-butoxyphenyl)-ethane
1-(4-(4-trans-Pentylcyclohexyl)-3-methylphenyl)-2-(4-butoxyphenyl)-ethane
1-(4-(4-trans-Pentylcyclohexyl)-2-methylphenyl)-2-(4-N-butylaminophenyl)-ethane
1-(4-(4-trans-Pentylcyclohexyl)-3-methylphenyl)-2-(4-N-butylaminophenyl)-ethane
1-(4-(4-trans-Pentylcyclohexyl)-2-methylphenyl)-2-(4-octanoylphenyl)-ethane
1-(4-(4-trans-Pentylcyclohexyl)-3-methylphenyl)-2-(4-octanoylphenyl)-ethane
1-(4-(4-trans-Pentylcyclohexyl)-2-methylphenyl)-2-(2-methyl4-pentylphenyl)-ethane
1-(4-(4-trans-Pentylcyclohexyl)-3-methylphenyl)-2-(2-methyl4-pentylphenyl)-ethane
1-(4-(4-trans-Pentylcyclohexyl)-2-methylphenyl)-2-(3-methyl4-pentylphenyl)-ethane
1-(4-(4-trans-Pentylcyclohexyl)-3-methylphenyl)-2-(3-methyl4-pentylphenyl)-ethane
1-(4-(4-trans-Pentylcyclohexyl)-2-methylphenyl)-2-(4-butoxy-2-methylphenyl)-ethane
1-(4-(4-trans-Pentylcyclohexyl)-3-methylphenyl)-2-(4-butoxy-2-methylphenyl)-ethane
1-(4-(4-trans-Pentylcyclohexyl)-2-methylphenyl)-2-(4-butoxy-3-methylphenyl)-ethane
1-(4-(4-trans-Pentylcyclohexyl)-3-methylphenyl)-2-(4-butoxy-3-methylphenyl)-ethane
1-(4-(4-trans-Pentylcyclohexyl)-2-methylphenyl)-2-(4-N-butylamino-2-methylphenyl)-ethane
1-(4-(4-trans-Pentylcyclohexyl)-3-methylphenyl)-2-(4-N-butylamino-2-methylphenyl)-ethane
1-(4-(4-trans-Pentylcyclohexyl)-2-methylphenyl)-2-(4-N-butylamino-3-methylphenyl)-ethane
1-(4-(4-trans-Pentylcyclohexyl)-3-methylphenyl)-2-(4-N-butylamino-3-methylphenyl)-ethane
1-(4-(4-trans-Pentylcyclohexvl)-2-methylphenyl)-2-(2-methyl-4-octanoyloxyphenyl)-ethane
1-(4-(4-trans-Pentylcyclohexyl)-3-methylphenyl)-2-(2-methyl-4-octanoyloxyphenyl)-ethane
1-(4-(4-trans-Pentylcyclohexyl)-2-methylphenyl)-2-(3-methyl-4-octanoyloxyphenyl)-ethane
1-(4-(4-trans-Pentylcyclohexyl)-3-methylphenyl)-2-(3-methyl-4-octanoyloxyphenyl)-ethane
1-(3,3'-Dimethyl-4'-pentylbiphenyl-4-yl)-2-(4-trans-pentylcyclohexyl)-ethane
1-(3,3'-Dimethyl-4'-octanoyloxybiphenyl-4-yl)-2-(4-transpentylcyclohexyl)-ethane
1-(4'-Butoxy-3,3'-dimethylbiphenyl-4-yl)-2-(4-trans-pentylcyclohexyl)-ethane
1-(4'-N-Butylamino-3,3'-dimethylbiphenyl-4-yl)-2-(4-transpentylcyclohexyl)-ethane
(3,3'-Dimethyl-4'-pentyl)-biphenyl-4-yl-(4-trans-pentylcyclohexyl)-methyl-ether
(3,3'-Dimethyl-4'-octanoyloxy)-biphenyl-4-yl-(4-transpentylcyclohexyl)-methyl-ether
(4'-Butoxy-3,3'-dimethyl)-biphenyl-4-yl-(4-trans-pentylcyclohexyl)-methyl-ether
(4'-N-Butylamino-3,3'-dimethyl)-biphenyl-4-yl-(4-transpentylcyclohexyl)-methyl-ether
1,4-bis-(4-trans-Propylcyclohexyl)-2-methyl-benzene
1,4-bis-(4-trans-Nonylcyclohexyl)-2-methyl-benzene
1-(4-trans-Nonylcyclohexyl)-4-(4-trans-propylcyclohexyl)-2-methyl-benzene
1-(4-trans-Nonylcyclohexyl)-4-(4-trans-propylcyclohexyl)-3-methyl-benzene
1-(4-trans-Propylcyclohexyl)-2-(4-(4-trans-propylcyclohexyl)-2-methylphenyl)-ethane
1-(4-trans-Propylcyclohexyl)-2-(4-(4-trans-propylcyclohexyl)-3-methylphenyl)-ethane
1-(4-trans-Propylcyclohexyl)-2-(4-(4-trans-nonylcyclohexyl)-2-methylphenyl)-ethane
1-(4-trans-Propylcyclohexyl)-2-(4-(4-trans-nonylcyclohexyl)-3-methylphenyl)-ethane
1-(4-trans-Nonylcyclohexyl)-2-(4-(4-trans-propylcyclohexyl)-2-methylphenyl)-ethane
1-(4-trans-Nonylcyclohexyl)-2-(4-(4-trans-propylcyclohexyl)-3-methylphenyl)-ethane
1-(4-trans-Nonylcyclohexyl)-2-(4-(4-trans-nonylcyclohexyl)-2-methylphenyl)-ethane
1-(4-trans-Nonylcyclohexyl)-2-(4-(4-trans-nonylcyclohexyl)-3-methylphenyl)-ethane
(4-trans-Propylcyclohexyl)-methyl-(4-(4-trans-propylcyclohexyl)-2-methyl)-phenyl-ether
(4-trans-Propylcyclohexyl)-methyl-(4-(4-trans-propylcyclohexyl)-3-methyl)-phenyl-ether
(4-trans-Propylcyclohexyl)-methyl-(4-(4-trans-nonylcyclohexyl)-2-methyl)-phenyl-ether
(4-trans-Propylcyclohexyl)-methyl-(4-(4-trans-nonylcyclohexyl)-3-methyl)-phenyl-ether
(4-trans-Nonylcyclohexyl)-methyl-(4-(4-trans-propylcyclohexyl)-2-methyl)-phenyl-ether
(4-trans-Nonylcyclohexyl)-methyl-(4-(4-trans-propylcyclohexyl)-3-methyl)-phenyl-ether
(4-trans-Nonylcyclohexyl)-methyl-(4-(4-trans-nonylcyclohexyl)-2-methyl)-phenyl-ether
(4-trans-Nonylcyclohexyl)-methyl-(4-(4-trans-nonylcyclohexyl)-3-methyl)-phenyl-ether
1,4-bis-(2-(4-trans-Propylcyclohexyl)-ethyl)-2-methyl-benzene
1,4-bis-(2-(4-trans-Nonylcyclohexyl)-ethyl)-2-methyl-benzene 1-(2-(4-trans-Nonylcyclohexyl)-ethyl)-4-(2-(4-trans-propylcyclohexyl)-ethyl)-2-methyl-benzene
1-(2-(4-trans-Nonylcyclohexyl)-ethyl)-4-(2-(4-trans-propylcyclohexyl)-ethyl-3-methyl-benzene
1,4-bis-(2-(4-trans-Propylcyclohexyl)-ethyl)-2,3-dimethylbenzene
1,4-bis-(2-(4-trans-Nonylcyclohexyl)-ethyl)-2,3-dimethylbenzene
1-(2-(4-trans-Nonylcyclohexyl)-ethyl)-4-(2-(4-trans-propylcyclohexyl)-ethyl)-2,3-dimethyl-benzene
1-(4'-trans-Pentyl-trans-bicyclohex-4-yl)-2-methyl-4-pentylbenzene
1-(4'-trans-Pentyl-trans-bicyclohex-4-yl)-3-methyl-4-pentylbenzene
1-(4'-trans-Pentyl-trans-bicyclohex-4-yl)-4-methyl-2-pentylbenzene
1-(4'-trans-Pentyl-trans-bicyclohex-4-yl)-4-butoxy-3-methylbenzene
1-(4'-trans-Pentyl-trans-bicyclohex-4-yl)-4-N-butylamino-2-methyl-benzene
1-(4'-trans-Pentyl-trans-bicyclohex-4-yl)-4-N-butylamino-3-methyl-benzene
1-(4'-trans-Pentyl-trans-bicyclohex-4-yl)-2-methyl-4-octanoyloxy-benzene
1-(4'-trans-Pentyl-trans-bicyclohex-4-yl)-3-methyl-4-octanoyloxy-benzene
1-(4'-trans-Pentyl-trans-bicyclohex-4-yl)-2-(2-methyl-4-pentylphenyl)-ethane
1-(4'-trans-Pentyl-trans-bicyclohex-4-yl)-2-(3-methyl-4-pentylphenyl)-ethane
1-(4'-trans-Pentyl-trans-bicyclohex-4-yl)-2-(4-butoxy-2-methylphenyl)-ethane
1-(4'-trans-Pentyl-trans-bicyclohex-4-yl)-2-(4-butoxy-3-methylphenyl)-ethane
1-(4'-trans-Pentyl-trans-bicyclohex-4-yl)-2-(4-N-butylamino-2-methylphenyl)-ethane
1-(4'-trans-Pentyl-trans-bicyclohex-4-yl)-2-(4-N-butylamino-3-methylphenyl)-ethane
1-(4'-trans-Pentyl-trans-bicyclohex-4-yl)-2-(2-methyl-4-octanoyloxyphenyl)-ethane
1-(4'-trans-Pentyl-trans-bicyclohex-4-yl)-2-(3-methyl-4-octanoyloxyphenyl)-ethane
(4'-trans-Pentyl-trans-bicyclohex-4-yl)-methyl-(2-methyl-4-pentyl)-phenyl-ether
(4'-trans-Pentyl-trans-bicyclohex-4-yl)-methyl-(3-methyl-4-pentyl)-phenyl-ether
(4'-trans-Pentyl-trans-bicyclohex-4-yl)-methyl-(2-methyl-4-octanoyloxy)-phenyl-ether
(4'-trans-Pentyl-trans-bicyclohex-4-yl)-methyl-(3-methyl-4-octanoyloxy)-phenyl-ether
(4'-trans-Pentyl-trans-bicyclohex-4-yl)-methyl-(4-butoxy-2-methyl)-phenyl-ether
(4'-trans-Pentyl-trans-bicyclohex-4-yl)-methyl-(4-butoxy-3-methyl)-phenyl-ether
(4'-trans-Pentyl-trans-bicyclohex-4-yl)-methyl-(4-N-butyl-amino-2-methyl)-phenyl-ether
(4'-trans-Pentyl-trans-bicyclohex-4-yl)-methyl-(4-N-butyl-amino-3-methyl)-phenyl-ether
5-(4-(4-trans-Pentylcyclohexyl)-2-methylphenyl)-2-heptylpyrimidine
5-(4-(4-trans-Pentylcyclohexyl)-3-methylphenyl)-2-heptylpyrimidine
2-(4-(4-trans-Pentylcyclohexyl)-2-methylphenyl)-5-heptylpyrimidine
2-(4-(4-trans-Pentylcyclohexyl)-3-methylphenyl)-5-heptylpyrimidine
2-(4-(4-trans-Pentylcyclohexyl)-2-methylphenyl)-5-butoxypyrimidine
2-(4-(4-trans-Pentylcyclohexyl)-3-methylphenyl)-5-butoxypyrimidine
5-(4-(2-(4-trans-Propylcyclohexyl)-ethyl)-2-methylphenyl)-2-propyl-pyrimidine
5-(4-(2-(4-trans-Propylcyclohexyl)-ethyl)-3-methylphenyl)-2-propyl-pyrimidine
5-(4-(2-(4-trans-Propylcyclohexyl)-ethyl)-2-methylphenyl)-2-nonyl-pyrimidine
5-(4-(2-(4-trans-Propylcyclohexyl)-ethyl)-3-methylphenyl)-2-nonyl-pyrimidine
5-(4-(2-(4-trans-Nonylcyclohexyl)-ethyl)-2-methylphenyl)-2-propyl-pyrimidine
5-(4-(2-(4-trans-Nonylcyclohexyl)-ethyl)-3-methylphenyl)-2-propyl-pyrimidine
5-(4-(2-(4-trans-Nonylcyclohexyl)-ethyl)-2-methylphenyl)-2-nonyl-pyrimidine
5-(4-(2-(4-trans-Nonylcyclohexyl)-ethyl)-3-methylphenyl)-2-nonyl-pyrimidine
5-(4-trans-Propylcyclohexylmethoxy)-2-methylphenyl)2-propyl-pyrimidine
5-(4-(4-trans-Propylcyclohexylmethoxy)-3-methylphenyl)-2-propyl-pyrimidine
5-(4-(4-trans-Propylcyclohexylmethoxy)-2-methylphenyl)-2-nonyl-pyrimidine
5-(4-(4-trans-Propylcyclohexylmethoxy)-3-methylphenyl)-2-nonyl-pyrimidine
5-(4-(4-trans-Nonylcyclohexylmethoxy)-2-methylphenyl)-2-propyl-pyrimidine
5-(4-(4-trans-Nonylcyclohexylmethoxy)-3-methylphenyl)-2-propyl-pyrimidine
5-(4-(4-trans-Nonylcyclohexylmethoxy)-2-methylphenyl)-2-nonyl-pyrimidine
5-(4-(4-trans-Nonylcyclohexylmethoxy)-3-methylphenyl)-2-nonyl-pyrimidine
2-(4-(2-(4-trans-Propylcyclohexyl)-ethyl)-2-methylphenyl)-5-propyl-pyrimidine
2-(4-(2-(4-trans-Propylcyclohexyl)-ethyl)-3-methylphenyl)-5-propyl-pyrimidine
2-(4-(2-(4-trans-Propylcyclohexyl)-ethyl)-2-methylphenyl)-5-nonyl-pyrimidine
2-(4-(2-(4-trans-Propylcyclohexyl)-ethyl)-3-methylphenyl)-5-nonyl-pyrimidine
2-(4-(2-(4-trans-Propylcyclohexyl)-ethyl)-2-methylphenyl)-5-butoxy-pyrimidine
2-(4-(2-(4-trans-Propylcyclohexyl)-ethyl)-3-methylphenyl)-5-butoxy-pyrimidine
2-(4-(2-(4-trans-Propylcyclohexyl)-ethyl)-2-methylphenyl)-5-octyloxy-pyrimidine
2-(4-(2-(4-trans-Propylcyclohexyl)-ethyl)-3-methylphenyl)-5-octyloxy-pyrimidine
2-(4-(2-(4-trans-Nonylcyclohexyl)-ethyl)-2-methylphenyl)-5-propyl-pyrimidine
2-(4-(2-(4-trans-Nonylcyclohexyl)-ethyl)-3-methylphenyl)-5-propyl-pyrimidine
2-(4-(2-(4-trans-Nonylcyclohexyl)-ethyl)-2-methylphenyl)-5-nonyl-pyrimidine
2-(4-(2-(4-trans-Nonylcyclohexyl)-ethyl)-3-methylphenyl)-5-nonyl-pyrimidine
2-(4-(2-(4-trans-Nonylcyclohexyl)-ethyl)-2-methylphenyl)-5-butoxy-pyrimidine
2-(4-(2-(4-trans-Nonylcyclohexyl)-ethyl)-3-methylphenyl)-5-butoxy-pyrimidine
2-(4-(2-(4-trans-Nonylcyclohexyl)-ethyl)-2-methylphenyl)-5-octyloxy-pyrimidine
2-(4-(2-(4-trans-Nonylcyclohexyl)-ethyl)-3-methylphenyl)-5-octyloxy-pyrimidine
2-(4-(4-trans-Propylcyclohexylmethoxy)-2-methylphenyl)-5-propyl-pyrimidine 2-(4-(4-trans-Propylcyclohexylmethoxy)-3-methyl-phenyl)-5-propyl-pyrimidine
2-(4-(4-trans-Propylcyclohexylmethoxy)-2-methyl-phenyl)-5-nonyl-pyrimidine
2-(4-(4-trans-Propylcyclohexylmethoxy)-3-methyl-phenyl)-5-nonyl-pyrimidine
2-(4-(4-trans-Propylcyclohexylmethoxy)-2-methyl-phenyl)-5-butoxy-pyrimidine
2-(4-(4-trans-Propylcyclohexylmethoxy)-3-methyl-phenyl)-5-butoxy-pyrimidine
2-(4-(4-trans-Propylcyclohexylmethoxy)-2-methyl-phenyl)-5-octyloxy-pyrimidine
2-(4-(4-trans-Propylcyclohexylmethoxy)-3-methyl-phenyl)-5-octyloxy-pyrimidine
2-(4-(4-trans-Nonylcyclohexylmethoxy)-2-methyl-phenyl)-5-propyl-pyrimidine
2-(4-(4-trans-Nonylcyclohexylmethoxy)-3-methyl-phenyl)-5-propyl-pyrimidine
2-(4-(4-trans-Nonylcyclohexylmethoxy)-2-methyl-phenyl)-5-nonyl-pyrimidine
2-(4-(4-trans-Nonylcyclohexylmethoxy)-3-methyl-phenyl)-5-nonyl-pyrimidine
2-(4-(4-trans-Nonylcyclohexylmethoxy)-2-methyl-phenyl)-5-butoxy-pyrimidine
2-(4-(4-trans-Nonylcyclohexylmethoxy)-3-methyl-phenyl)-5-butoxy-pyrimidine
2-(4-(4-trans-Nonylcyclohexylmethoxy)-2-methyl-phenyl)-5-octyloxy-pyrimidine
2-(4-(4-trans-Nonylcyclohexylmethoxy)-3-methyl-phenyl)-5-octyloxy-pyrimidine
4,4'-bis-(4-trans-Propylcyclohexyl)-2-methyl-biphenyl
4,4'-bis-(4-trans-Propylcyclohexyl)-3-methyl-biphenyl
4,4'-bis-(4-trans-Propylcyclohexyl)-3,3'-dimethyl-biphenyl
4,4'-bis-(4-trans-Propylcyclohexyl)-2,3'-dimethyl-biphenyl
4,4'-bis-(4-trans-Nonylcyclohexyl)-2-methyl-biphenyl
4,4'-bis-(4-trans-Nonylcyclohexyl)-3-methyl-biphenyl
4,4'-bis-(4-trans-Nonylcyclohexyl)-2,3'-dimethyl-biphenyl
4,4'-bis-(4-trans-Nonylcyclohexyl)-3,3'-dimethyl-biphenyl
4-(4-trans-Nonylcyclohexyl)-4'-(4-trans-propylcyclohexyl)-2-methyl-biphenyl
4-(4-trans-Nonylcyclohexyl)-4'-(4-trans-propylcyclohexyl)-3-methyl-biphenyl
4-(4-trans-Nonylcyclohexyl)-4'-(4-trans-propylcyclohexyl)-2'-methyl-biphenyl
4-(4-trans-Nonylcyclohexyl)-4'-(4-trans-propylcyclohexyl)-2,3'-methyl-biphenyl
4-(4-trans-Nonylcyclohexyl)-4'-(4-trans-propylcyclohexyl)-2,3'-dimethyl-biphenyl
4-(4-trans-Nonylcyclohexyl)-4'-(4-trans-propylcyclohexyl)-3,3'-dimethyl-biphenyl
4-(4-trans-Nonylcyclohexyl)-4'-(4-trans-propylcyclohexyl)-3,3'-dimethyl-biphenyl
4,4'-bis-(2-(4-trans-Propylcyclohexyl)-ethyl)-2,3'-dimethylbiphenyl
4'-bis-(2-(4-trans-Propylcyclohexyl)-ethyl)-2,3'-dimethylbiphenyl
4,4'-bis-(2-(4-trans-Nonylcyclohexyl)-ethyl)-2,3'-dimethylbiphenyl
4,4'-bis-(2-(4-trans-Nonylcyclohexyl)-ethyl)-3,3'-dimethylbiphenyl
4-(2-(4-Nonylcyclohexyl)-ethyl)-4'-(2-(4-trans-propylcyclohexyl)-ethyl)-2,3'-dimethyl-biphenyl
4-(2-(4-trans-Nonylcyclohexyl)-ethyl)-4'-(2-(4-trans-propylcyclohexyl)-ethyl)-2',3-dimethyl-biphenyl
4-(2-(4-trans-Nonylcyclohexyl)-ethyl)-4-(2-(4-trans-propylcyclohexyl)-ethyl)-3,3'-dimethyl-biphenyl
4,4'-bis-(4-trans-Propylcyclohexylmethoxy)-2,3'-dimethyl-biphenyl
4,4'-bis-(4-trans-Propylcyclohexylmethoxy)-3,3'-dimethyl-biphenyl
4,4'-bis-(4-trans-Nonylcyclohexylmethoxy)-2,3'-dimethyl-biphenyl
4,4'-bis-(4-trans-Nonylcyclohexylmethoxy)-3,3'-dimethyl-biphenyl
4-(4-trans-Nonylcyclohexylmethoxy)-4'-(4-trans-propylcyclohexylmethoxy)-2,3'-dimethyl-biphenyl
4-(4-trans-Nonylcyclohexylmethoxy)-4'-(4-trans-propylcyclohexylmethoxy)-2'3-dimethyl-biphenyl
4-(4-trans-Nonylcyclohexylmethoxy)-4'-(4-trans-propylcyclohexylmethoxy)-3,3'-dimethyl-biphenyl
4-(4'-trans-Pentyl-trans-bicyclohex-4-yl)-2,3'-dimethyl-4'-pentyl-biphenyl
4-(4'-trans-Pentyl-trans-bicyclohex-4-yl)-2',3-dimethyl-4'-pentyl-biphenyl
4-(4'-trans-Pentyl-trans-bicyclohex-4-yl)-3,3'-dimethyl-4'-pentyl-biphenyl
4-(4'-trans-Pentyl-trans-bicyclohex-4-yl)-4'-butoxy-2,3'-dimethyl-biphenyl
4-(4'-trans-Pentyl-trans-bicyclohex-4-yl)-4'-butoxy-2',3-dimethyl-biphenyl
4-(4'-trans-Pentyl-trans-bicyclohex-4-yl)-4'-butoxy-3,3'-dimethyl-biphenyl
4-(4'-trans-Pentyl-trans-bicyclohex-4-yl)-4'-N-butylamino-2,3'-dimethyl-biphenyl
4-(4'-trans-Pentyl-trans-bicyclohex-4-yl)-4'-N-butylamino-2',3'-dimethyl-biphenyl
4-(4'-trans-Pentyl-trans-bicyclohex-4-yl)-4'-N-butylamino-3,3'-dimethyl-biphenyl
4-(4'-trans-Pentyl-trans-bicyclohex-4-yl)-2,3'-dimethyl-4'-octanoyloxy-biphenyl
4-(4'-trans-Pentyl-trans-bicyclohex-4-yl)-2',3-dimethyl-4'-octanoyloxy-biphenyl
4-(4'-trans-Pentyl-trans-bicyclohex-4-yl)-3,3'-dimethyl-4'-octanoyloxy-biphenyl
4-(4'-trans-Pentyl-trans-bicyclohex-4-yl)-2-methyl-4'-pentylbiphenyl
4-(4'-trans-Pentyl-trans-bicyclohex-4-yl)-3-methyl-4'-pentylbiphenyl
4-(4'-trans-Pentyl-trans-bicyclohex-4-yl)-2-methyl-4'-octanoyloxy-biphenyl
4-(4'-trans-Pentyl-trans-bicyclohex-4-yl)-3-methyl-4'-octanoyloxy-biphenyl
4-(4'-trans-Pentyl-trans-bicyclohex-4-yl)-4'-butoxy-2-methylbiphenyl
4-(4'-trans-Pentyl-trans-bicyclohex-4-yl)-4'-butoxy-3-methylbiphenyl
4-(4'-trans-Pentyl-trans-bicyclohex-4-yl)-4'-N-butyloxy-2-methyl-biphenyl
4-(4'-trans-Pentyl-trans-bicyclohex-4-yl)-4'-N-butyloxy-3-methyl-biphenyl
1-(4'-trans-bicyclohex-4-yl)-2-(2-methyl-4'-pentylbiphenyl-4-yl)-ethane
1-(4'-trans-Pentyl-trans-bicyclohex-4-yl)-2-(3-methyl-4'-pentylbiphenyl-4-yl)-ethane
1-(4'-trans-Pentyl-trans-bicyclohex-4-yl)-2-(2,3'-dimethyl-4'-pentylbiphenyl-4-yl)-ethane
1-(4'-trans-Pentyl-trans-bicyclohex-4-yl)-2-(2',3-dimethyl-4'-pentylbiphenyl-4-yl)-ethane
1-(4'-trans-Pentyl-trans-bicyclohex-4-yl)-2-(3,3'-dimethyl-4'-pentylbiphenyl-4-yl)-ethane
1-(4'-trans-Pentyl-trans-bicyclohex-4-yl)-2-(4'-butoxy-2-methylbiphenyl-4-yl)-ethane 1-(4'-trans-Pentyl-trans-bicyclohex-4-yl)-2-(4'-butoxy-3-methylbiphenyl-4-yl)-ethane
1-(4'-trans-Pentyl-trans-bicyclohex-4-yl)-2-(4'-butoxy-2,3'-dimethylbiphenyl-4-yl)-ethane
1-(4'-trans-Pentyl-trans-bicyclohex-4-yl)-2-(4'-butoxy-2',3-dimethylbiphenyl-4-yl)-ethane
1-(4'-trans-Pentyl-trans-bicyclohex-4-yl)-2-(4'-butoxy-3,3'-dimethylbiphenyl-4-yl)-ethane
1-(4'-trans-Pentyl-trans-bicyclohex-4-yl)-2-(4'-N-butylamino-2-methylbiphenyl-4-yl)-ethane
1-(4'-trans-Pentyl-trans-bicyclohex-4-yl)-2-(4'-N-butylamino-3-methylbiphenyl-4-yl)-ethane
1-(4'-trans-Pentyl-trans-bicyclohex-4-yl)-2-(4'-N-butylamino-2,3'-methylbiphenyl-4-yl)-ethane
1-(4'-trans-Pentyl-trans-bicyclohex-4-yl)-2-(4'-N-butylamino-2,3'-dimethylbiphenyl-4-yl)-ethane
1-(4'-trans-Pentyl-trans-bicyclohex-4-yl)-2-(4'-N-butylamino-3,3'-dimethylbiphenyl-4-yl)-ethane
1-(4'-trans-Pentyl-trans-bicyclohex-4-yl)-2-(2-methyl-4'-octanoyloxybiphenyl-4-yl)-ethane
1-(4'-trans-Pentyl-trans-bicyclohex-4-yl)-2-(3-methyl-4'-octanoyloxybiphenyl-4-yl)-ethane
1-(4'-trans-Pentyl-trans-bicyclohex-4-yl)-2-(2,3'-dimethyl-4'-octanoyloxybiphenyl-4'-yl)-ethane
1-(4'-trans-Pentyl-trans-bicyclohex-4-yl)-2-(2,3'-dimethyl-4'-octanoyloxybiphenyl-4-yl)-ethane
1-(4'-trans-Pentyl-trans-bicyclohex-4-yl)-2-(3,3'-dimethyl-4'-octanoyloxybiphenyl-4-yl)-ethane
(4'-trans-Pentyl-trans-bicyclohex-4-yl)-methyl-(2-methyl-4'-pentyl)-biphenyl-4-yl-ether
(4'-trans-Pentyl-trans-bicyclohex-4-yl)-methyl-(3-methyl-4'-pentyl)-biphenyl-4-yl-ether
(4'-trans-Pentyl-trans-bicyclohex-4-yl)-methyl-(2,3'-dimethyl-4'-pentyl)-biphenyl-4-yl-ether
(4'-trans-Pentyl-trans-bicyclohex-4-yl)-methyl-(2',3-dimethyl-4'-pentyl)-biphenyl-4-yl-ether
(4'-trans-Pentyl-trans-bicyclohex-4-yl)-methyl-(3,3'-dimethyl-4'-pentyl)-biphenyl-4-yl-ether
(4'-trans-Pentyl-trans-bicyclohex-4-yl)-methyl-(4'-butoxy-2-methyl)-biphenyl-4-yl-ether
(4'-trans-Pentyl-trans-bicyclohex-4-yl)-methyl-(4'-butoxy-3-methyl)-biphenyl-4-yl-ether
(4'-trans-Pentyl-trans-bicyclohex-4-yl)-methyl-(4'-butoxy-2,3'-dimethyl)-biphenyl-4-yl-ether
(4'-trans-Pentyl-trans-bicyclohex-4-yl)-methyl-(4'-butoxy-2'3-dimethyl)-biphenyl-4-yl-ether
(4'-trans-Pentyl-trans-bicyclohex-4-yl)-methyl-(4'-butoxy-3,3'-dimethyl)-biphenyl-4-yl-ether
(4'-trans-Pentyl-trans-bicyclohex-4-yl)-methyl-(4'-N-butyl-amino-2-methyl)-biphenyl-4-yl-ether
(4'-trans-Pentyl-trans-bicyclohex-4-yl)-methyl-(4'-N-butyl-amino-3-methyl)-biphenyl-4-yl-ether
(4'-trans-Pentyl-trans-bicyclohex-4-yl)-methyl-(4'-N-butylamino-2,3'-dimethyl)-biphenyl-4-yl-ether
(4'-trans-Pentyl-trans-bicyclohex-4-yl)-methyl-(4'-N-butylamino-2,3'-dimethyl)-biphenyl-4-yl-ether
(4'-trans-Pentyl-trans-bicyclohex-4-yl)-methyl-(4'-N-butylamino-3,3'-dimethyl)-biphenyl-4-yl-ether
(4'-trans-Pentyl-trans-bicyclohex-4-yl)-methyl-(2-methyl-4'-octanoyloxy)-biphenyl-4-yl-ether
(4'-trans-Pentyl-trans-bicyclohex-4-yl)-methyl-(3-methyl-4'-octanoyloxy)-biphenyl-4-yl-ether
(4'-trans-Pentyl-trans-bicyclohex-4-yl)-methyl-(2,3'-dimethyl-4'-octanoyloxy)-biphenyl-4-yl-ether
(4'-trans-Pentyl-trans-bicyclohex-4-yl)-methyl-(2',3-dimethyl-4'-octanoyloxy)-biphenyl-4-yl-ether
(4'-trans-Pentyl-trans-bicyclohex-4-yl)-methyl-(3,3'-dimethyl-4'-octanoyloxy)-biphenyl-4-yl-ether.

What is claimed as new and sought to be protected by letters patente of the United States is:

1. Anisotropic compound having the formula

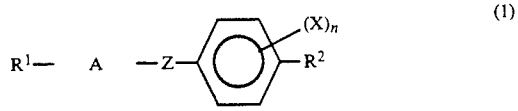

wherein A is a cyclic radical of formula (11)

Z is selected from the group consisting of a single bond and —CH$_2$CH$_2$— group, n is 1 or 2

X is selected from the group consisting of fluorine, chlorine, bromine, and iodine, R$^1$ and R$^2$ are selected from the group consisting of C$_1$-C$_{12}$-alkyl, C$_1$-C$_{12}$-alkoxy, C$_1$-C$_{12}$-alkanoyloxy and C$_1$-C$_{12}$-alkylamino and cyclic groups of the formulae

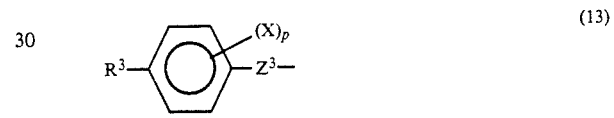

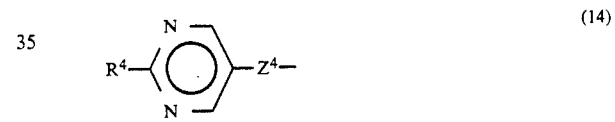

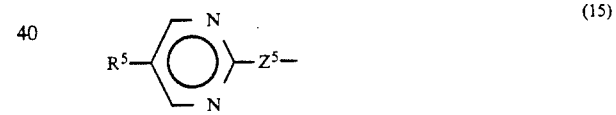

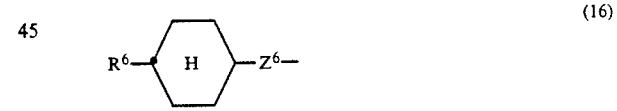

wherein R$^3$ through R$^6$ are selected from the group consisting of C$_1$-C$_{12}$-alkyl, C$_1$-C$_{12}$-alkoxy, C$_1$-C$_{12}$-alkanoyloxy and C$_1$-C$_{12}$-alkylamino, Z$^3$ through Z$^6$ represent a group which is selected from the group consisting of a single bond, a —CH$_2$CH$_2$-group, a methyleneoxy group and an oxymethylene group, X has the meaning given above and p is 0, 1, or 2, with the proviso that none of the above aromatic radicals (13), (14) or (15) is directly bonded to the C-atom of a methyleneoxy or oxymethylene group.

2. The compound of claim 1 having the formula

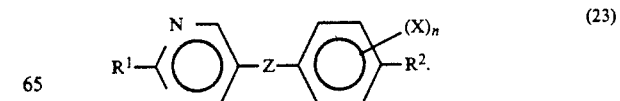

3. The compound of claim 1 having the formula

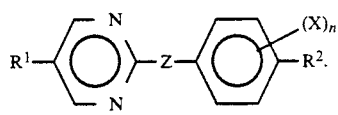

4. The compound of claim 1 having the formula

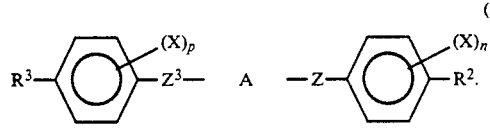

5. The compound of claim 1 having the formula

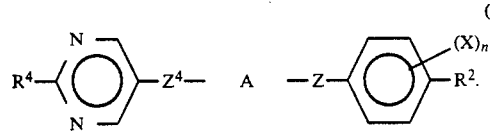

6. The compound of claim 6 having the formula

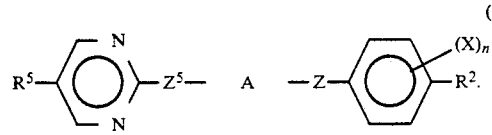

7. The compound of claim 1 having the formula

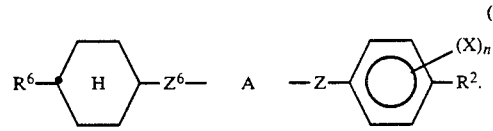

8. The compound of claim 7 having the formula

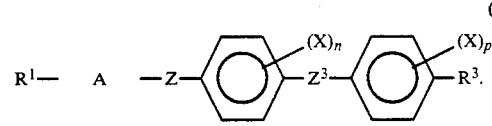

9. The compound of claim 8 having the formula

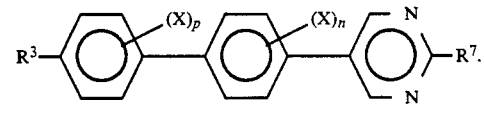

10. The compound of claim 8 having the formula

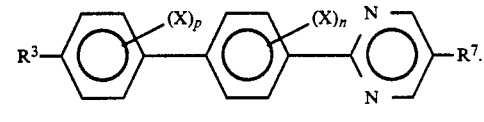

11. The compound of claim 8 having the formula

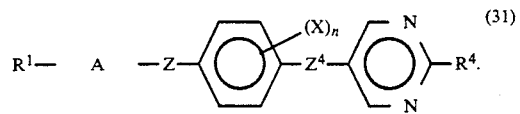

12. The compound of claim 1 having the formula

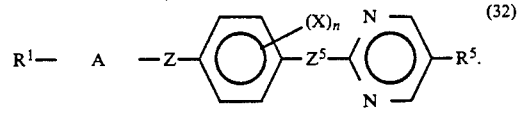

13. The compound of claim 9 having the formula

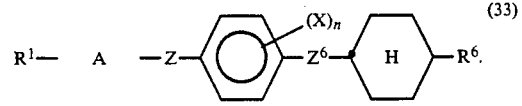

14. The compound of claim 13 having the formula

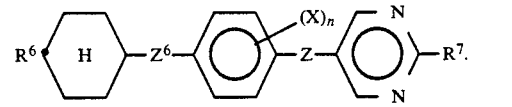

15. The compound of claim 13 having the formula

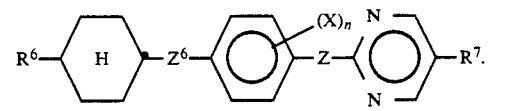

16. The compound of claim 10 wherein Z is a single bond.

17. The compound of claim 1, wherein N=1.

18. The compound of claim 1, wherein at least one of $R^1$ and $R^2$ is alkyl, alkoxy, alkanoyloxy or alkylamino, the alkyl portion of which is branched.

19. The compound of claim 18, wherein said branched alkyl portion is chiral.

20. The compound of claim 1, wherein one of $R^1$ and $R^2$ is $C_1$-$C_{12}$-alkyl or $C_1$-$C_{12}$-alkoxy.

21. The compound of claim 1, wherein one of $R^1$ and $R^2$ is a cyclic group of formula (13), (14), (15) or (16).

22. The compound of claim 21, wherein $R^3$ through $R^6$ are $C_1$-$C_{12}$-alkyl, $C_1$-$C_{12}$-alkoxy or $C_1$-$C_{12}$-alkanoyloxy.

23. The compound of claim 21, wherein $Z^3$ through $Z^6$ are a —$CH_2CH_2$-group or a single bond.

24. The compound of claim 21, wherein one of $R^1$ and $R^2$ is a cyclic group of formula (13) and p is 0.

25. The compound of claim 24, wherein $Z^3$ is a single bond.

26. The compound of claim 21, wherein one of $R^1$ and $R^2$ is a cyclic group of formula (16) and $R^6$ is $C_1$-$C_{12}$-alkyl.

27. The compound of claim 26, wherein $Z^6$ is —$CH_2CH_2$-group, a methyleneoxy group or a single bond.

* * * * *